(12) United States Patent
Florescu et al.

(10) Patent No.: US 8,614,572 B2
(45) Date of Patent: Dec. 24, 2013

(54) INTEGRATED MAGNETIC FIELD GENERATION AND DETECTION PLATFORM

(75) Inventors: Octavian Florescu, Berkeley, CA (US); Bernhard E. Boser, Berkeley, CA (US); Moritz Mattmann, Oberaegeri (CH)

(73) Assignee: The Regents of the University of California, Oakland, CA (US)

( * ) Notice: Subject to any disclaimer, the term of this patent is extended or adjusted under 35 U.S.C. 154(b) by 457 days.

(21) Appl. No.: 12/837,429

(22) Filed: Jul. 15, 2010

(65) Prior Publication Data

US 2011/0018532 A1 Jan. 27, 2011

Related U.S. Application Data

(63) Continuation of application No. PCT/US2009/031155, filed on Jan. 15, 2009.

(60) Provisional application No. 61/021,861, filed on Jan. 17, 2008.

(51) Int. Cl.
*G01R 33/06* (2006.01)

(52) U.S. Cl.
USPC ........... 324/251; 324/204; 324/252; 324/228; 324/202; 436/526; 436/518; 436/524; 436/149

(58) Field of Classification Search
USPC .............. 324/204, 252, 228, 202, 313, 251; 436/526, 518, 524, 149
See application file for complete search history.

(56) References Cited

U.S. PATENT DOCUMENTS

| | | | |
|---|---|---|---|
| 7,046,002 B1 * | 5/2006 | Edelstein | 324/244 |
| 7,425,455 B2 | 9/2008 | Fukumoto et al. | |
| 7,582,490 B2 * | 9/2009 | Golovchenko et al. | 438/10 |
| 2002/0028456 A1 * | 3/2002 | Mansky et al. | 435/6 |
| 2004/0033627 A1 * | 2/2004 | Aytur et al. | 436/526 |
| 2004/0126899 A1 * | 7/2004 | Lee et al. | 436/518 |
| 2005/0130296 A1 * | 6/2005 | Pisharody et al. | 435/287.2 |

(Continued)

FOREIGN PATENT DOCUMENTS

| | | |
|---|---|---|
| EP | 1 469 311 A1 | 10/2004 |
| JP | 2009-511894 A | 3/2009 |

(Continued)

OTHER PUBLICATIONS

Aytur, T. et al.—"An Immunoassay Platform Based on CMOS Hall Sensors"—Solid State Sensor, Actuator and Microsystems Workshop, Hilton Head Island, SC, Jun. 206, 2002, pp. 126-129.

(Continued)

*Primary Examiner* — Huy Q Phan
*Assistant Examiner* — Temilade S Rhodes-Vivour
(74) *Attorney, Agent, or Firm* — John P. O'Banion

(57) ABSTRACT

An integrated magnetic field generation and detection platform is described that is capable of manipulating and detecting individual magnetic particles, such as spherical superparamagnetic beads, and providing biosensing functionality. The platform is implemented in an integrated circuit, a portion of the surface of which is functionalized with one or more biochemical agents that binds tightly (i.e., specifically) with a target analyte. The magnetic beads are similarly functionalized with one or more biochemical agents that that bind specifically with the target analyte. When a sample is introduced, magnetic beads that specifically bind to the integrated circuit can be separated from non-specifically bound beads and detected.

52 Claims, 21 Drawing Sheets

(56) References Cited

U.S. PATENT DOCUMENTS

| | | | |
|---|---|---|---|
| 2006/0170529 | A1* | 8/2006 | Shoji .......................... 338/32 R |
| 2006/0194327 | A1 | 8/2006 | Kahlan et al. |
| 2008/0191688 | A1 | 8/2008 | Kahlman et al. |
| 2009/0009156 | A1 | 1/2009 | Duric |
| 2009/0184706 | A1 | 7/2009 | Duric et al. |
| 2009/0278534 | A1 | 11/2009 | Kahlman |
| 2010/0060265 | A1 | 3/2010 | Nieuwenhuis et al. |

FOREIGN PATENT DOCUMENTS

| | | | |
|---|---|---|---|
| JP | 2009-539100 | A | 11/2009 |
| KR | 10-2004-0068968 | A | 8/2004 |
| KR | 10-2004-0075011 | A | 8/2004 |
| KR | 10-2006-0054351 | A | 5/2006 |
| WO | 9852043 | A1 | 11/1998 |
| WO | 200114591 | A1 | 3/2001 |
| WO | 2003067258 | A1 | 8/2003 |
| WO | 2005010527 | A1 | 2/2005 |
| WO | 2005022154 | A1 | 3/2005 |
| WO | 2005047864 | A2 | 5/2005 |
| WO | 2005085850 | A1 | 9/2005 |
| WO | 2006018811 | A1 | 2/2006 |
| WO | 2006134546 | A2 | 12/2006 |
| WO | 2007010368 | A1 | 1/2007 |
| WO | 2007029192 | A1 | 3/2007 |
| WO | 2007042958 | A2 | 4/2007 |
| WO | WO 2007042958 | A2 * | 4/2007 |
| WO | 2007105140 | A2 | 9/2007 |
| WO | 2007129275 | A2 | 11/2007 |
| WO | 2007129277 | A2 | 11/2007 |
| WO | 2007132372 | A1 | 11/2007 |
| WO | 2007132384 | A2 | 11/2007 |
| WO | 2007141691 | A2 | 12/2007 |
| WO | 2008001261 | A2 | 1/2008 |
| WO | 2008001266 | A2 | 1/2008 |
| WO | WO 2008001266 | A2 * | 1/2008 |

OTHER PUBLICATIONS

Aytur, T. et al.—"A novel magnetic bead bioassay platform using a microchip-based sensor for infectious disease diagnosis"—Jour. of Immunological Methods 314, 2006, pp. 21-29.

Baselt D.R. et al.—"A biosensor based on magnetoresistance technology"—Biosensors & Bioelectronics 13, 1998, pp. 731-739.

Lagae, L. et al.—"On-chip manipulation and magnetization assessment of magnet bead ensembles by integrated spin-valve sensors"—Jour. of Applied Physics, vol. 91, No. 10, May 15, 2002, pp. 7445-7447.

Liu, C. et al.—"Manipulation of magnetic particles on chip by magnetophoretic actuation and dielectrophoretic levitation"—Applied Physics Letter 90, 2007, pp. 174109-1-184109-3.

Besse, P.A. et al.—"Detection of a single magnetic microbead using a miniaturized silicon Hall sensor"—Applied Physics Letters, vol. 80, No. 22, Jun. 3, 2002, pp. 4199-4201.

Graham, D.L. et al.—"Single magnetic microsphere placement and detection on-chip: using current line designs with integrated spin valve sensors: biotechnological applications"—Jour. of Applied Physics, vol. 91, No. 10, May 15, 2002, pp. 7786-7788.

WIPO, International Publication No. WO 2009/091926 dated Jul. 23, 2009, including international search report and written opinion issued on Jul. 30, 2009, from counterpart PCT Application No. PCT/US2009/031155, pp. 1-63.

European Patent Office, extended European search report dated Jan. 14, 2011, including claims, from counterpart European patent application No. 09702685.0, pp. 1-12.

State Intellectual Property Office of the P.R.C., Patent Application 200980105452.3, First Action issued on Oct. 10, 2011 (pp. 1-8), with English translation (pp. 9-19) and claims (pp. 20-25), counterpart to PCT/US2009/031155, claiming priority to U.S. Appl. No. 61/021,861.

European Patent Office, related European patent appplication No. 09 702 685.0, Office Action issued Jun. 21, 2012 (pp. 1-6), with claims examined (pp. 7-14), counterpart to PCT/US2009/031155, claiming priority to U.S. Appl. No. 61/021,861, pp. 1-14.

State Intellectual Property Office of the P.R.C., related Chinese patent application No. 200980105452.3, Second Office Action issued on May 9, 2012 (pp. 1-7), with English translation (pp. 8-16), and claims as examined (pp. 17-22), pp. 1-22.

Florescu, O. et al.—"Hall Sensor Based CMOS Immunosensor"—Nov. 30, 2007, pp. 1-2; downloaded from URL: http://www.eecs.berkeley.edu/Research/Projects/2008/105253.html on Jan. 20, 2012.

Florescu, O. et al.—"Fully integrated detection of single magnetic beads in complementary metal-oxide-semiconductor"—Jour. of Applied Physics, vol. 103, Feb. 19, 2008, pp. 046101-1 to 046101-3.

European Patent Office, related European patent application 09 702 685.0, Office Action issued Jan. 30, 2012 (pp. 1-6), with claims examined (pp. 7-14), counterpart to PCT/US09/031155, claiming priority to U.S. Appl. No. 61/021,861, pp. 1-14.

Florescu, O. et al.—"Hall Sensor-Based CMOS ImmunoSensor"—UC Berkeley Library, Oct. 10, 2007, pp. 1-11.

Florescu, O. et al.—"Semi-Annual Research Report: Hall Sensor-Based ImmunoSensor"—UC Berkeley Library, Oct. 10, 2007, pp. 1-2.

European Patent Office, related European patent application 09 702 685.0, Office Action issued Sep. 16, 2011 (pp. 1-7), with claims examined (pp. 8-13), counterpart to PCT/US09/031155, claiming priority to U.S. Appl. No. 61/021,861, pp. 1-13.

State Intellectual Property Office of the P.R.C., Patent Application 200980105452.3, Third Action issued on Oct. 22, 2012, including English translation summary (pp. 1-3), claims examined (pp. 3-7), and Original Office Action in Chinese language (pp. 8-15), counterpart to PCT/US2009/031155, claiming priority to U.S. Appl. No. 61/021,861, all references cited in current office action were submitted with prior IDS filed on Jun. 29, 2011.

European Patent Office, Office Action issued Jan. 24, 2013 (pp. 1-5) for corresponding European Patent.

Octavian Florescu, "Hall-sensor based magnetic immunosensor. BEB17," Recent BSAC Achievments, Fall 2006, published online Sep. 20, 2006, University of California, Berkeley, one page.

Florescu, Octavian, "Hall Sensor Based CMOS ImmunoSensor," University of California Berkeley, published Sep. 2007, one page.

State Intellectual Property Office of the P.R.C., Fourth Office Action issued for corresponding Chinese Patent Application 200980105452.3 on May 14, 2013, English translation summary (pp. 1-2), claims examined (pp. 3-6), and Original Office Action in Chinese (pp. 7-11), counterpart to PCT/US2009/031155, claiming priority to U.S. Appl. No. 61/021,861; pp. 1-11.

Japanese Patent Office, Notification of Reasons for Refusal (Office Action), for corresponding Japanese Patent Application No. 2010-543257 (International Patent Application No. PCT/US2009/031155) English translation (pp. 1-3), claims examined (pp. 4-10) and original Office Action in Japanse (pp. 11-13) pp. 1-13.

* cited by examiner

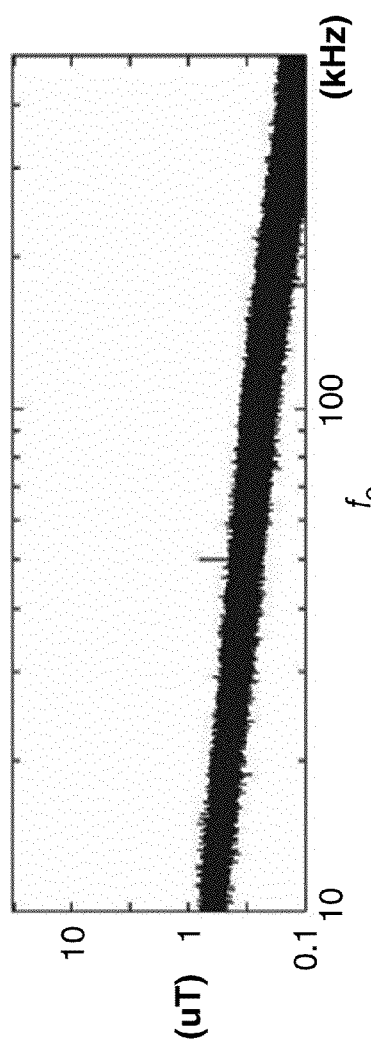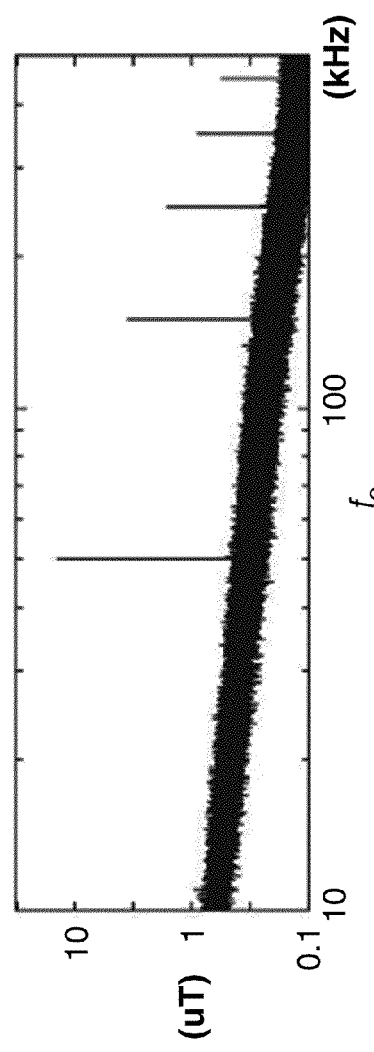
FIG. 4A
FIG. 4B

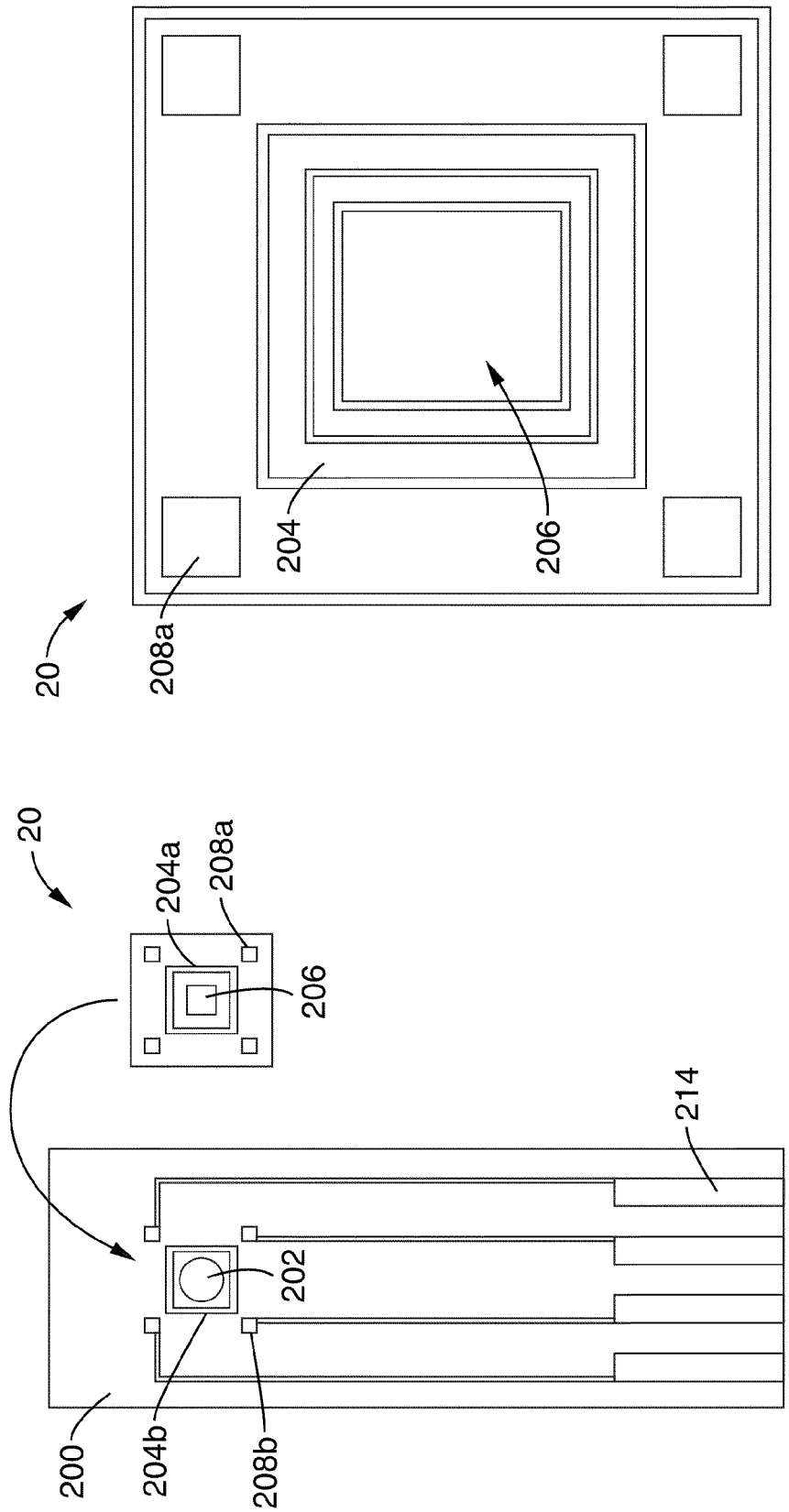

INTEGRATED MAGNETIC FIELD GENERATION AND DETECTION PLATFORM

CROSS-REFERENCE TO RELATED APPLICATIONS

This application claims priority from, and is a 35 U.S.C. §111(a) continuation of, co-pending PCT international application serial number PCT/US2009/031155 filed on Jan. 15, 2009, incorporated herein by reference in its entirety, which claims priority from U.S. provisional application Ser. No. 61/021,861 filed on Jan. 17, 2008, incorporated herein by reference in its entirety.

This application is also related to PCT International Publication No. WO 2009/091926 published on Jul. 23, 2009, incorporated herein by reference in its entirety.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

BACKGROUND OF THE INVENTION

1. Field of the Invention

This invention pertains generally to detecting the presence of target analytes, and more particularly to an integrated magnetic field generation and detection platform.

2. Description of Related Art

As baby-boomers in developed nations retire and as the ranks of new healthcare recipients in developing nations swell, new medical systems are needed to weather the storm of rising healthcare costs. In particular, Point-of-Care (POC) technologies have the potential to keep costs at bay by enabling affordable preventative diagnostics and personal chronic disease monitoring. Many of these POC technologies use detection schemes that rely on the specific marking of target analyte with labels, such as catalytic enzymes, optical markers or magnetic beads. The latter are very useful as labels for bio-assay applications because (a) cells exhibit few if any magnetic properties, b) signals from magnetic beads are stable with time, (c) magnetic detection functions regardless of the opacity of the sample, and (d) magnetic labeling provides added functionality such as magnetic filtration and manipulation.

BRIEF SUMMARY OF THE INVENTION

The present invention, according to one aspect, comprises an integrated magnetic field generation and detection platform. The platform is capable of manipulating and detecting individual magnetic particles, such as spherical super-paramagnetic beads, and providing biosensing functionality. Another aspect of the invention is an integrated circuit having, in one beneficial embodiment, means for generating a magnetic separation field, means for generating a magnetic concentration/magnetization field, and means for detecting a magnetic field. In one exemplary mode of use, magnetic beads are first manipulated using the separation field generating means and/or the concentration/magnetization field generating means, then magnetized using the concentration/magnetization field generating means, and then detected using the field detecting means.

In another embodiment, an integrated circuit apparatus comprises a substrate having an exposed surface; field detecting means embedded in the substrate beneath the substrate surface; and concentration/magnetization field generating means embedded in the substrate and positioned between the field detecting means and the substrate surface.

In another embodiment, an integrated circuit apparatus comprises a substrate having a trench with an exposed surface, the trench having a sidewall with an upper ridge portion; field detecting means embedded in the substrate beneath the substrate surface; concentration/magnetization field generating means embedded in the substrate and positioned between the field detecting means and the substrate surface; and separation field generating means in the upper ridge portion of the sidewall.

In another embodiment, an integrated circuit apparatus comprises a substrate having a plurality of trenches, each trench having an exposed surface area and a sidewall with an upper ridge portion; field detecting means embedded in the substrate beneath the substrate surface; and concentration/magnetization field generating means embedded in the substrate and positioned between the field detecting means and the substrate surface.

In another embodiment, the integrated circuit is a component of a biosensor device. In one exemplary mode of use, at least a portion of the surface of the integrated circuit is functionalized by coating it with a biochemical agent that binds tightly (i.e., specifically) with a target analyte. The magnetic beads are similarly coated or conjugated with one or more biochemical agents that that bind specifically with the target analyte. The sample is introduced and the target analyte binds to the functionalized surface of the integrated circuit. The magnetic beads are introduced and they either bind specifically to the surface of the trench via the biochemical complex involving the target antigen, or non-specifically. The magnetic beads may bind to the analyte first, before they settle to the surface of the substrate, at which point the analyte also binds to the substrate, thereby tethering the bead to the surface. The non-specifically bound beads can then be removed by on-chip magnetic washing forces, and the remaining specifically bound beads can be detected by magnetic field detecting means integrated beneath the surface of the substrate. This biosensor can therefore be used to determine the concentration of infectious disease agents in blood or serum.

In various embodiments, the concentration/magnetization field generating means can comprise a plurality of microcoils, a current line (e.g., conductor), or other elements that generate a magnetic field, positioned between the surface of the substrate and the field detecting means.

In one embodiment, the concentration/magnetization field generating means comprises a plurality of individual magnetic field generating elements, and the field detecting means comprises a plurality of individual magnetic field detecting elements, wherein each magnetic field generating element is paired with a magnetic field detecting element to create a stacked unit cell.

In various embodiments, the field detecting means can comprise a plurality of Hall sensors, variable inductance wires, or other elements that can sense a magnetized object.

In various embodiments, the separation field generating means can be placed laterally apart from the concentration/magnetization field generating means either in the same plane or in a plane above the concentration/magnetization field generating means.

In various embodiments, the separation field generating means can comprise current lines (e.g., conductors) or other elements that generate a magnetic field.

In various embodiments, at least a portion of the exposed surface area of the substrate is functionalized with a biochemical agent that binds with a target analyte.

In various embodiments, at least a portion of the unit cells are addressable.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawings which are for illustrative purposes only:

FIG. 1 schematically shows an integrated micro-coil/Hall sensor pair according to an embodiment of the invention with a magnetic bead positioned above the Hall sensor/micro-coil pair for context.

FIG. 2 is a schematic plan view of two micro-coil/Hall sensor elements of the type shown in FIG. 1, implemented in a loose array.

FIG. 3 is a schematic diagram of a micro-coil/Hall sensor pair from an active sensor array and a "dummy" micro-coil/Hall sensor pair from a reference array, both connected to an on-chip amplifier (OCA) and analog to digital converter (ADC) and digital signal processor (DSP), for rejection of common-mode applied fields from the coils to be rejected while the differential induced field from the bead is amplified.

FIG. 4 is the spectrum of the output of the ADC of FIG. 3 measured with a 1 Hz noise bandwidth, directly after auto-zeroing (upper graph) and after application of the bead (lower graph).

FIG. 17 is a bottom plan view of a printed circuit board configured for supporting an integrated circuit according to the present invention for biological sensing, with the integrated circuit shown exploded away from the circuit board.

FIG. 18 is a top plan view of an embodiment of the integrated circuit shown in FIG. 17.

Figure 24:
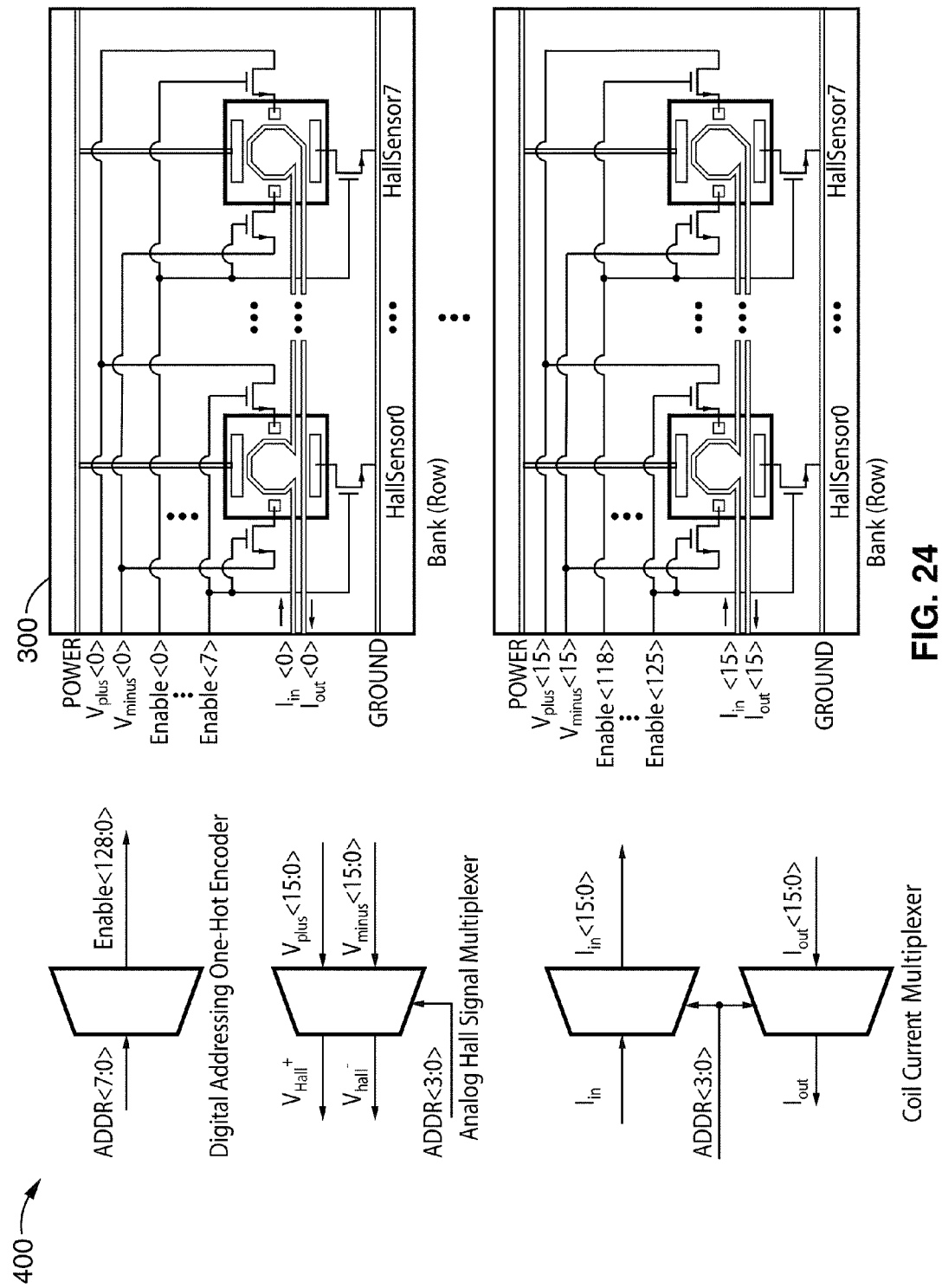
FIG. 24 is an electrical circuit diagram of sixteen banks of the micro-coil/Hall sensor elements shown in FIG. 23, with addressing schemes shown on the left.
Figure 25:
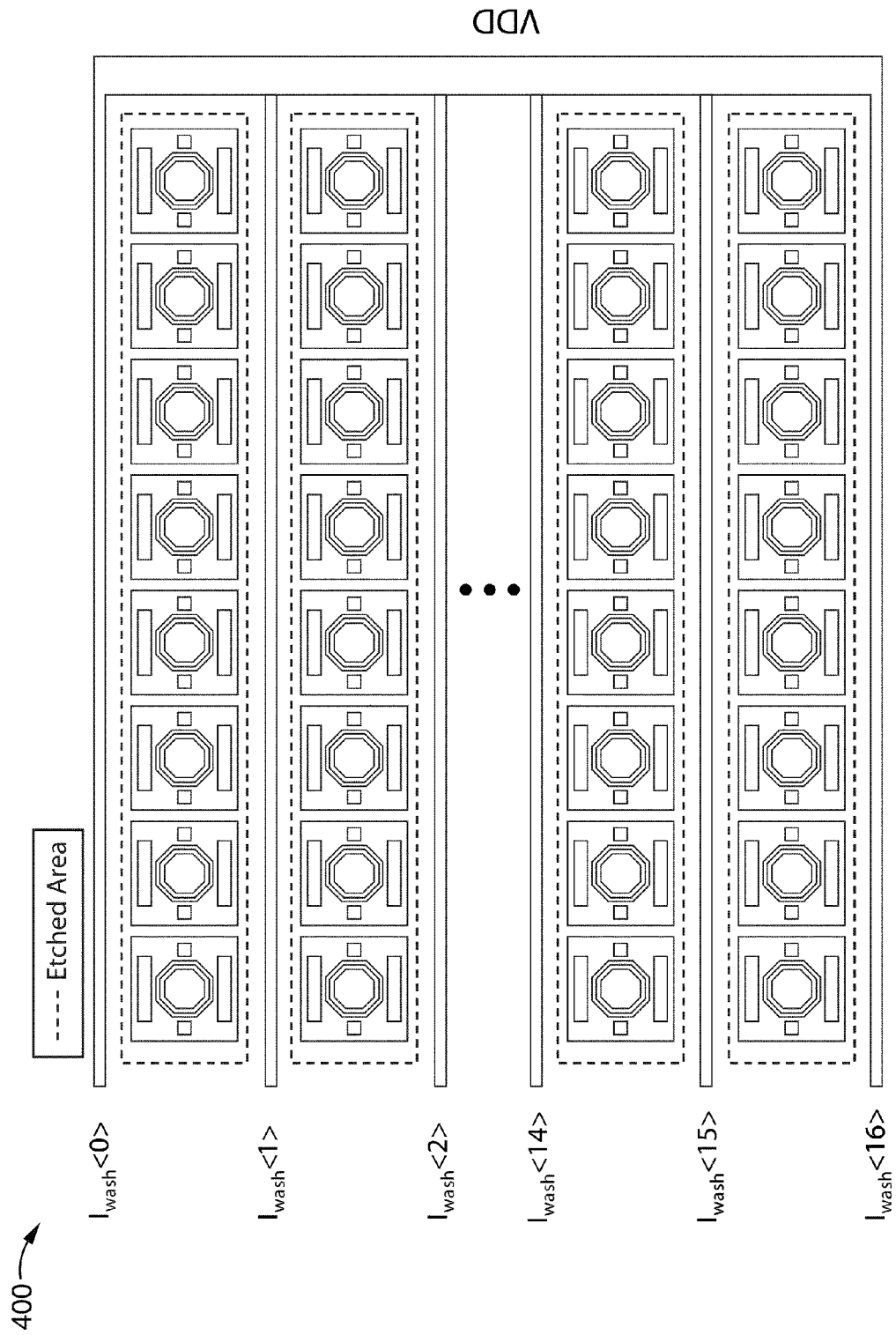

FIG. 25 schematically shows the sixteen banks of micro-coil/Hall sensor elements of FIG. 24 with current lines for generating the magnetic separation forces being placed adjacent to the banks of Hall sensors, and with the dashed lines showing the areas of micro-coil/sensor element banks.

DETAILED DESCRIPTION OF EMBODIMENTS OF THE INVENTION

Figure 2:
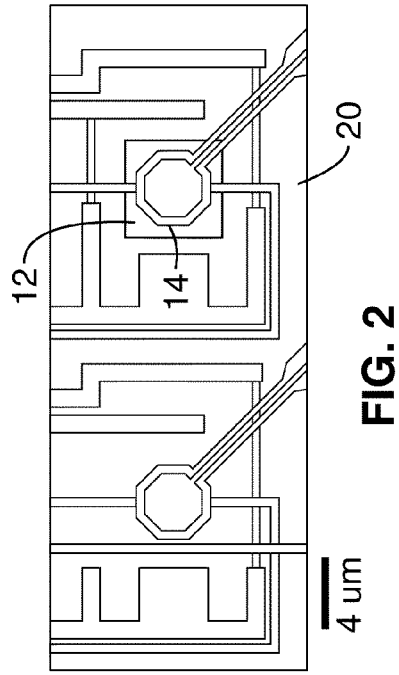
Figure 1:
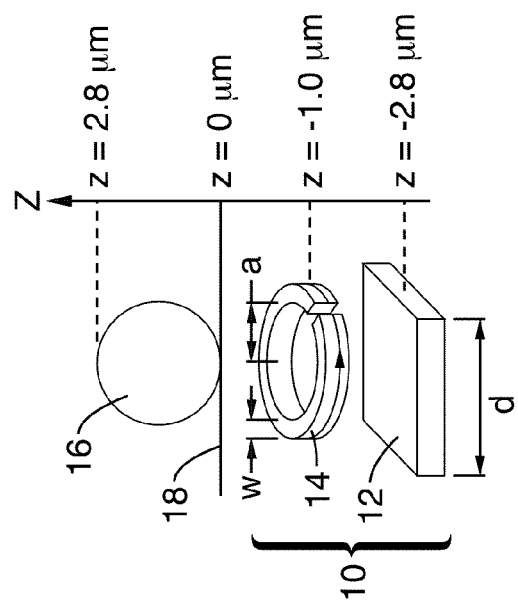

Referring first to FIG. 1 and FIG. 2, magnetic bead detection according to the present invention is based on embedding, beneath an exposed surface area of a substrate, (i) means for detecting a magnetic field, and (ii) means for generating a magnetic concentration/magnetization field between the field detecting means and the substrate surface. In the embodiment shown, the field detecting means and concentration/magnetization field generating means form a unit cell 10, which in this embodiment comprises a Hall sensor 12 stacked beneath a micro-coil 14. The micro-coil and Hall sensor, respectively, polarize and detect an individual super-paramagnetic bead 16 at the surface 18 of a CMOS integrated circuit (IC) 20 into which the micro-coil/Hall sensor pair are integrated. In one embodiment, the micro-coils are single turn current loops having an inner radius a and line width w, and the Hall sensors are n-well square planar sensors having side dimensions d and thickness t. Each micro-coil and Hall sensor in a unit cell is preferably positioned coaxially along the z-axis as illustrated, with the micro-coil stacked above the Hall sensor and positioned closest to the surface of the integrated circuit.

In this regard, the z-component of the micro-coil's applied magnetic field can be described by the off-axis field of a current loop as follows:

$$B_{applied}(z) = \frac{\mu_o I_{coil}}{2\pi\sqrt{(a+r)^2 + z^2}} \times \left[ E(k) \frac{a^2 - r^2 - z^2}{(a+r)^2 + z^2 - 4ar} + K(k) \right] \quad (1)$$

where $\mu_o$, is the permeability of free space, $I_{coil}$ is the current through the coil, r is the distance from the center of the coil to the point of observation, E(k) and K(k) are the complete elliptical integral functions of the $1^{st}$ and $2^{nd}$ kind and k is given by:

$$k = \frac{4ra}{(a+r)^2 + z^2} \quad (2)$$

According to equations (1) and (2), 10 mA of current through the micro-coil will produce a magnetic field $B_{applied}(z_{bead})$=800 μT at the center of the bead and an average field $B_{applied}(z_{Hall})$=750 μT across the Hall sensor contacts.

The induced magnetization field of the bead, $B_{bead}$, is approximated by equation (3) below:

$$B_{bead} = \frac{\mu_o}{4\pi} \cdot \frac{3(r \cdot m_{bead})r - (r \cdot r)m_{bead}}{r^5} \quad (3)$$

where r is the vector from the point of observation to the center of the bead. $m_{bead}$ is the bead's magnetic moment, given by $m_{bead}=\chi_b V_b B_{applied}(z_{bead})z$, where $\chi_b$ and $V_b$ are the bead's magnetic susceptibility and volume. As can be seen from equation (3), the bead's induced magnetization field decays with the cube of the distance r, so the dielectric layer above the micro-coil/Hall sensor pair is etched back using conventional techniques. For $B_{applied}(z_{bead})$=800 μT, equation (3) estimates the z-component of the average induced magnetization field to be $B_{bead,z}$=10.2 μT across the contacts of the Hall sensor.

The equation for the Hall sensor voltage as a function of the z-component of the magnetic field is given by:

$$V_H = G_H \mu_o \frac{W_{Hall}}{L_{Hall}} B_z \quad (4)$$

where $W_{Hall}$ and $L_{Hall}$ are the width and length of the Hall plate, in this case both equal to d, and where $G_H$ is the Hall effect geometric factor. The calculated Hall sensitivity of 34V/AT is in line with measurement results for uniform fields, but a decreased sensitivity was noted for the highly non-uniform field from the coil.

For a more accurate value of the expected applied field from the coil and the magnetization field from the bead, the conditions shown in FIG. 1 were simulated using the research edition of MagNet by Infolytica. Table 1 gives the calculated, simulated and measured z-component of the applied coil field and bead magnetization field, observed from the plane of the Hall sensor. As seen in Table 1, the measured applied field from the coil is 50× larger than the induced field from the bead. To mitigate this undesirable dynamic range constraint, a differential architecture was employed, which subtracts the signal of a reference Hall sensor with no bead from the signal of a Hall sensor with a bead. This configuration is illustrated in FIG. 3, which is a schematic diagram of a micro-coil/Hall sensor pair 10a from a sensor array and a "dummy" or "reference" micro-coil/Hall sensor pair 10b from a reference array, both of which are connected to an on-chip amplifier (OCA) 100 and an off-chip 16-Bit analog to digital converter (ADC) 102 followed by digital signal processor (DSP) 104.

Figure 3:
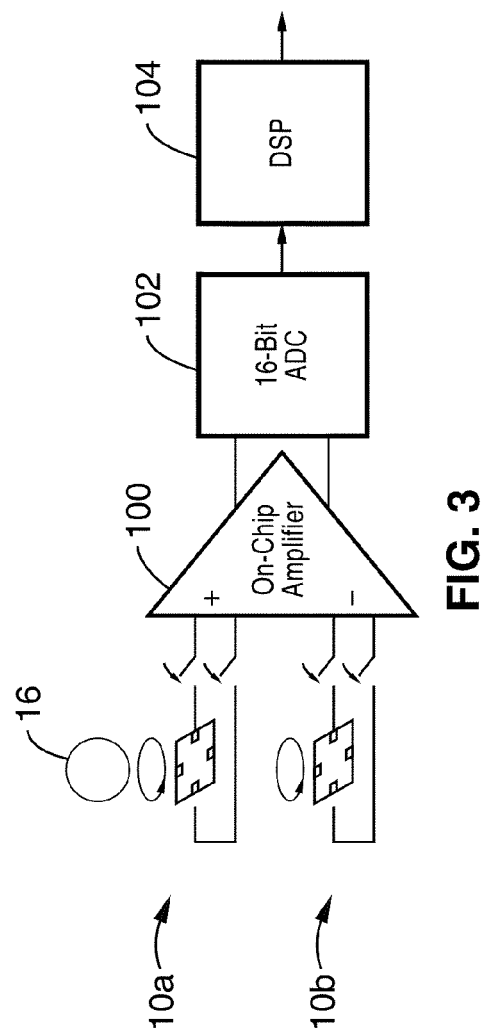

The configuration in FIG. 3 allows the common-mode applied fields from the coils to be rejected while the differential induced field from the bead, detected by the Hall sensor in pair 10a, is amplified. For further attenuation of the common-mode applied fields, a calibration feedback loop sets the current through micro-coil in pair 10b such that the output of the OCA 100 is zeroed out. The feedback loop applies an additional current in the reference coil to cancel out any residual field signal due to mismatch. The entire detection system noise is dominated by the 1/f noise of the OCA 100 with a spot noise of 300 nT/√Hz at the detection frequency of 50 kHz. After amplification, the output is digitized by the off-chip ADC 102 and processed by DSP 104.

In one embodiment, before the beads are applied, the system calibrates itself by auto-zeroing the output of the OCA 100 with the fundamental, $f_o$, of a 10 mA, 50 kHz square current wave through the micro-coils. In a manufacturing paradigm, this internal self calibration could be performed on the factory floor since the system does not suffer from appreciable drift. Alternatively, this self calibration can be performed immediately before patient use. Once the system has been calibrated, it is ready for detection. In our experiments, the beads were desiccated on the surface of the IC and then were individually micro-manipulated over the Hall sensors. The same square current wave that was used for calibration is sent through the coils and the new value of the fundamental at $f_o$ is recorded.

FIG. 4, which presents measurements from the Hall sensors directly after calibration and after a bead has been applied, shows that this system is capable of detecting individual magnetic beads with 33 dB of SNR for a 1 Hz noise bandwidth (i.e. for an integration time τ=1 s). FIG. 4 is the spectrum of the output of the ADC directly after auto-zeroing (upper graph) and after application of the bead (lower graph).

Figure 5:
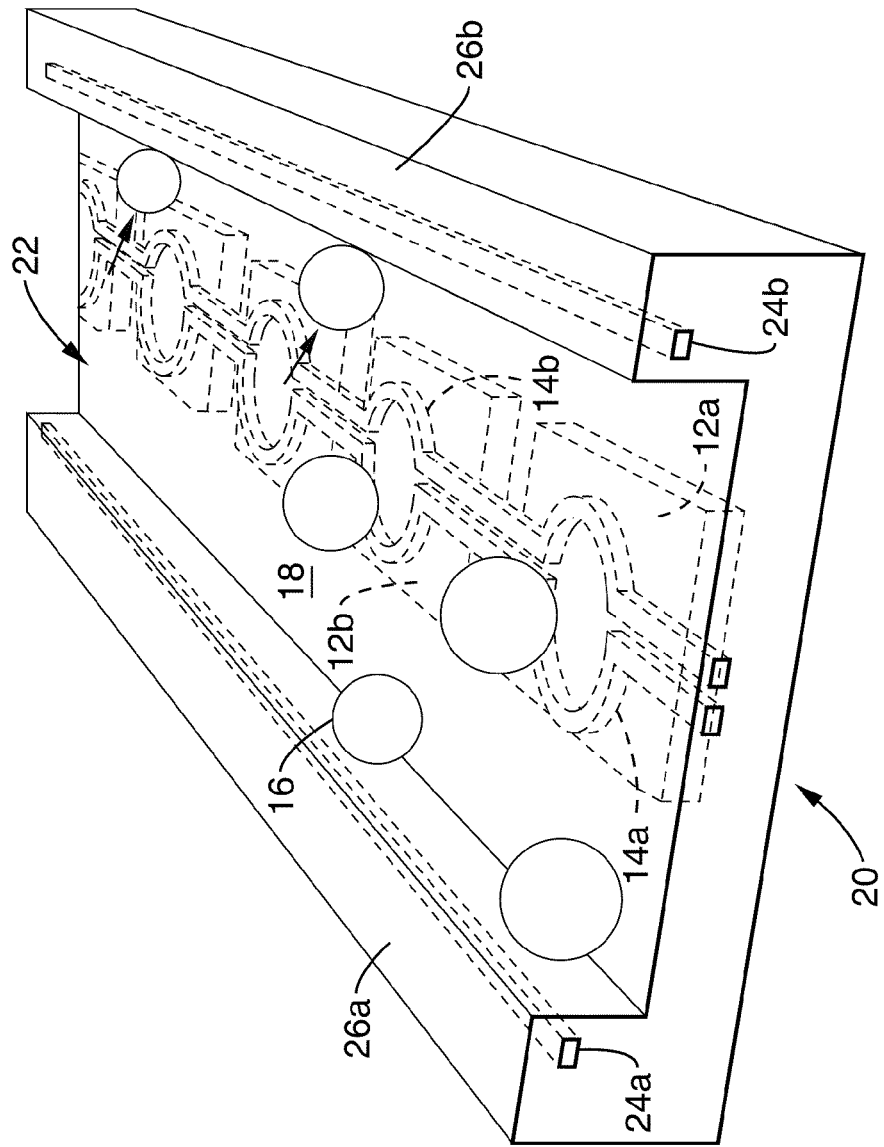
FIG. 5 is a perspective view of an array of integrated adjacent micro-coil/Hall sensor elements positioned in a row along the bottom of an etched trench with current lines along its ridges for integrated magnetic separation of magnetic beads, and showing a plurality of beads positioned above the micro-coil/Hall sensor elements for context.

Referring now to FIG. 5 and FIG. 6, an example of the fabrication of an embodiment of an IC 20 is illustrated. FIG. 5 shows a single row of interconnected micro-coil/Hall sensor unit cells 10 embedded beneath the bottom surface 18 of an etched trench 22, and separation field generating means in the form of current lines (electrical conductors) 24a, 24b embedded along the upper ridge portions of sidewalls 26a, 26b. Each micro-coil and Hall sensor in a unit cell is preferably positioned coaxially along the z-axis as illustrated, with the micro-coil vertically stacked above the Hall sensor and positioned closest to the exposed surface 18 of the trench 22. FIG. 5 also shows a plurality of beads 16 positioned above the micro-coil/Hall sensor elements for context. FIG. 6A is a cross-sectional view of IC 20 after conventional CMOS fabrication on an Si/SiO₂ substrate, but prior to the post-processing which creates trench 22. In this embodiment, the Hall sensors 12 are embedded in the Si layer 28 and the micro-coils 14 are embedded in the SiO₂ layer 30.

To reduce distance from the Hall sensors to the beads, we used a directional plasma etch to remove most of the $SiO_2$ 30 from above the micro-coil/Hall sensor area. This creates the trench 22 in the CMOS substrate. The top of the trench is determined by a protective top metal layer 32 and corresponds to the original surface of the IC (FIG. 6A) minus the dielectric etched during post processing described below with reference to FIG. 6B through FIG. 6E. The bottom of the trench is determined by a metal etch stop layer 34 placed directly above the metal micro-coils 14. The metal current lines 24 are integrated along the upper ridge portions of sidewalls 26a, 26b of the trenches at a location where magnetic forces generated when current runs through the current lines will be sufficient to manipulate and pull magnetic beads away from the sensor area and toward the sides of the trench. In this embodiment, the current lines 30 are positioned approximately 2.5 μm above the bottom of the trench to accommodate approximately 2.8 μm diameter beads. The sidewalls of the trench begin at approximately 15 μm from the outer edge of the micro-coils; thus, the trench width is approximately 34.2 μm in this example.

Figure 6A:
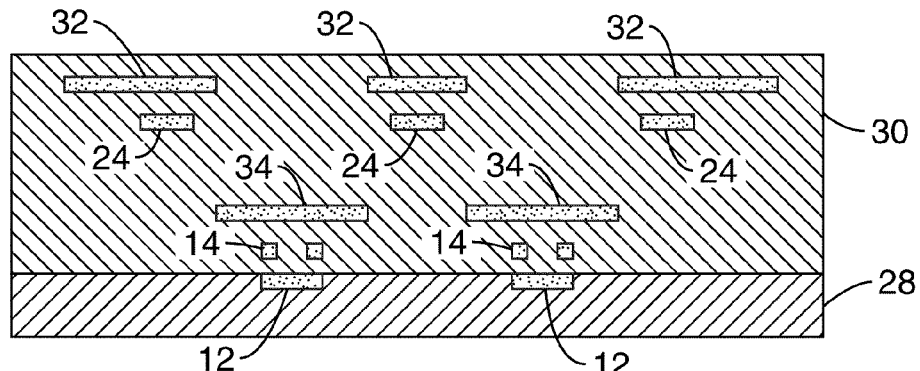
FIG. 6A through FIG. 6E is a cross-sectional flow diagram showing an embodiment of a reactive ion etching process used in fabrication of the integrated circuit shown in FIG. 5.
Figure 6B:
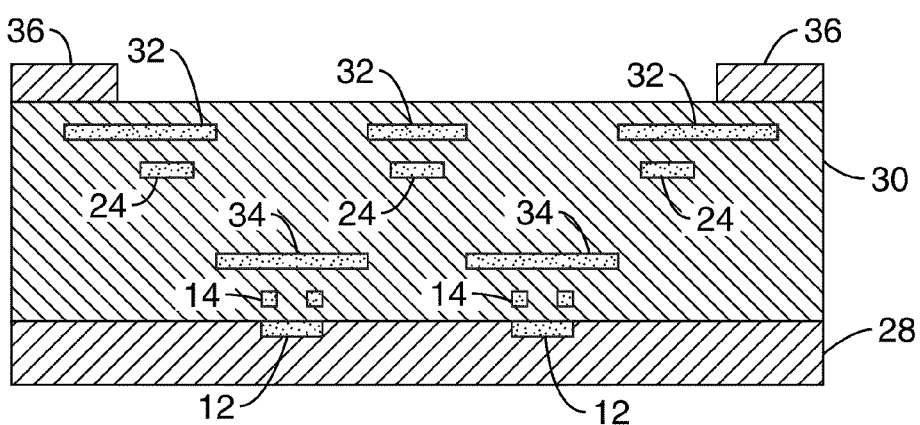
Figure 6C:
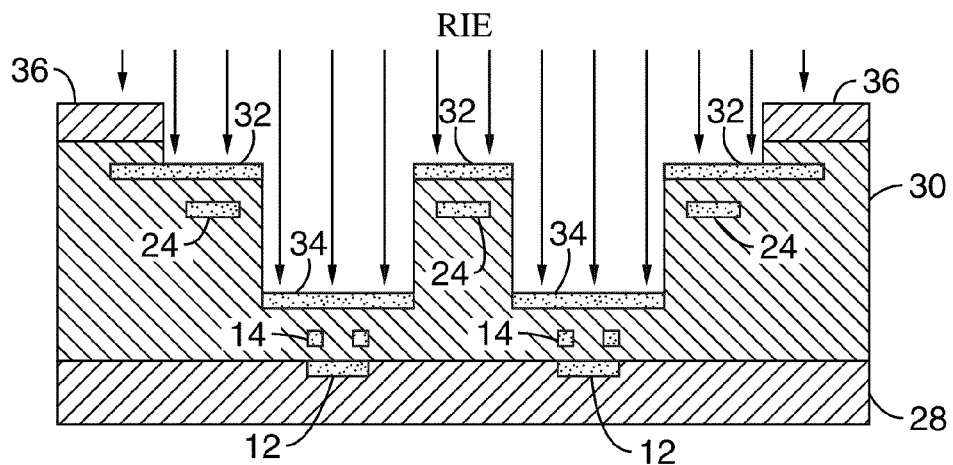
Figure 6D:
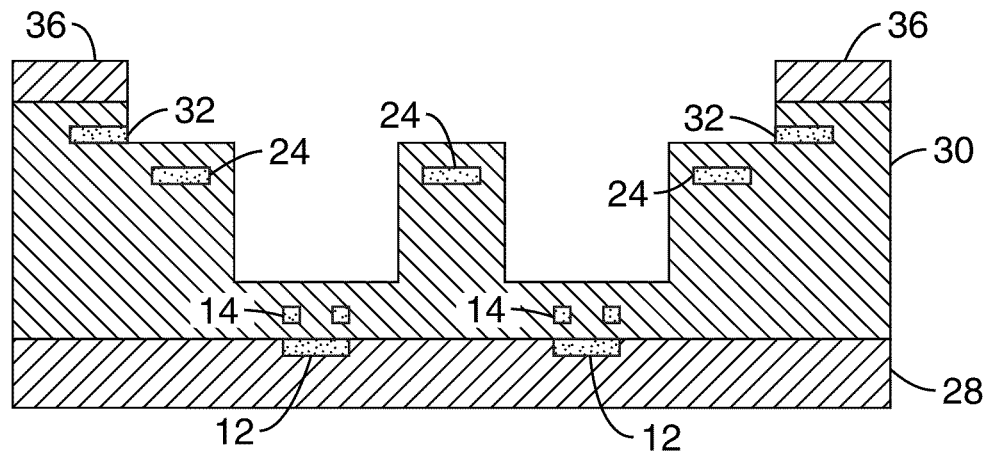
Figure 6E:
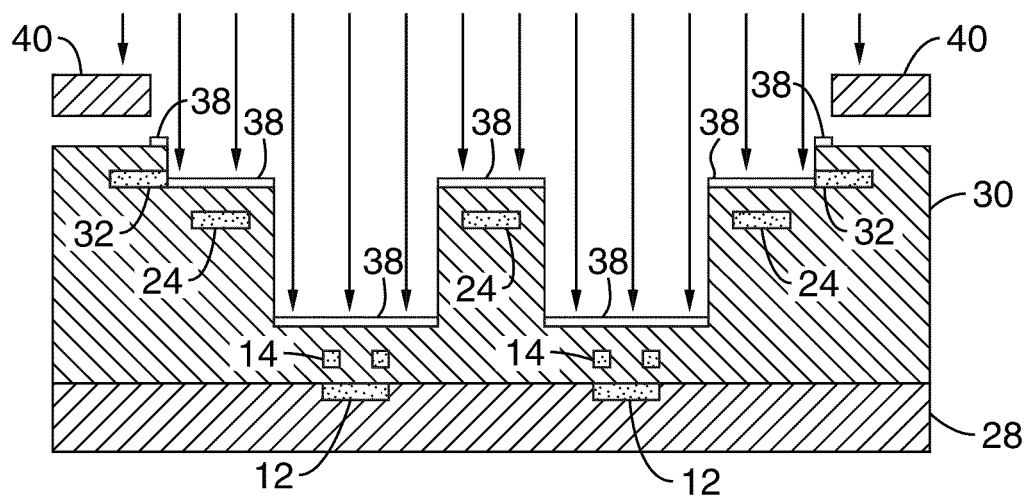

Post-processing of the IC shown in FIG. 6A generally proceeds as illustrated in FIG. 6B through FIG. 6E. In FIG. 6B, photoresist 36 is spun on and patterned to expose the sensor area. The connection pads and all other circuitry are protected by the photoresist. FIG. 6C shows $SiO_2$ reactive ion etching (RIE). Here, the photoresist 36, top metal 32 placed above the current lines 24, and metal 34 placed above the micro-coils 14 are used as the etch stop to the RIE. In FIG. 6D, an aluminum etch is used to remove the etch stop metal layer 34. The metal 32 that remains after the aluminum etch can safely remain since it is not electrically connected to IC and served only to define the trench and protect the current lines from washing. Finally, in FIG. 6E, a chromium seed layer and gold substrate layer 38 is evaporated through a hard mask (e.g., shadow mask) 40. This hard mask 40 allows the chromium and gold to settle only on the sensor area. In this embodiment, the photoresist is removed before the gold is evaporated onto the CMOS IC through a shadow mask 40. In another embodiment, the photoresist can be used as a lift-off mask for gold deposition to omit the shadow mask altogether. Trenching is now complete and the IC 20 is ready to be functionalized.

Referring again to FIG. 3 and the related discussion, a reference sensor array would be processed in a similar manner, except that the dielectric in the reference array would not be etched back to create a trench. Therefore, the sensors would never have a bead above them.

Example

To test the above-described configuration, we embedded micro-coils approximately 1.0 μm below the bottom of the trench in the lowest CMOS metallization layer, and we embedded Hall sensors approximately 2.8 μm below the micro-coils. The micro-coils that we used were single turn current loops having an inner radius $a=1.7$ μm, a line width $w=0.5$ μm, and an outer diameter of 4.2 μm. The Hall sensors that we used were n-well square planar sensors having side dimensions $d=4.7$ μm and thickness $t=1$ μm. For optimal performance, power consumption and packing density, our calculations showed that the overall sizes of the micro-coils, the Hall sensors and the beads should all be approximately the same, and in this experiment were 4 μm. We found that the micro-coils were capable of generating fields of up to 800 μT for 10 mA of current, and that the Hall sensors exhibited a sensitivity of 34V/AT for a 2 mA bias current. Using a differential amplifier, single spherical magnetic beads having a diameter of approximately 2.8 μm, were detected with 33 dB of SNR for a 1 Hz noise bandwidth.

In the embodiments described above, the concentration/magnetization field generating means comprises a plurality of individual magnetic field generating elements (e.g., micro-coils), and the field detecting means comprises a plurality of individual magnetic field detecting elements (e.g., Hall sensors), wherein each micro-coil is paired with a Hall sensor to create a stacked unit cell. It will be appreciated, however, that the configuration of the invention is not limited to that which is described above. For example, the concentration/magnetization field generating means can comprise a current line (e.g., conductor) or other element that generates a magnetic field, positioned between the surface of the substrate and the field detecting means. Furthermore, the field detecting means can comprise a variable inductance wire or other element that can sense a magnetized object. Also, not only can the separation field generating means be implemented in the form of a current line placed in the upper ridge of a trench sidewall as previously described, but alternatively, the separation field generating means can be placed laterally apart from the concentration/magnetization field generating means in the same plane rather than in a plane above the concentration/magnetization field generating means. The separation field generating means can also be used to magnetize the magnetic beads at an arbitrary frequency which obviates the need for the concentration/magnetization field generating means. The current through the separation field generating means can be changed arbitrarily as well.

Integrated circuits according to the present invention are particularly well suited for biosensing applications. For such applications, the integrated circuit and magnetic beads can be adapted to specifically (e.g., biologically) bind to target analytes. For example, the trench surface of the integrated circuit would be coated with one or more biochemical agents that binds tightly (i.e., specifically) with the target analyte. The magnetic beads would similarly be coated or conjugated with one or more biochemical agents that that bind specifically with the target analyte. For testing, we have employed monodispersed M280 Dynal beads of 2.8 μm in diameter that were functionalized with a streptadivin coating. These particular beads have been well characterized and are known to be effective as reporting agents.

When the sample is introduced into the sensor area, the target analyte binds to the surface of the integrated circuit. When the magnetic beads are introduced, they will either bind specifically to the functionalized surface of the substrate via the biochemical complex involving the target antigen, or non-specifically. The non-specifically bound beads can then be removed by on-chip magnetic washing forces, and the remaining specifically bound beads can be detected by the magnetic sensors integrated beneath the surface of the trench. In general, it is possible to detect immobilized magnetic particles including non-specifically bound beads.

Figure 7:
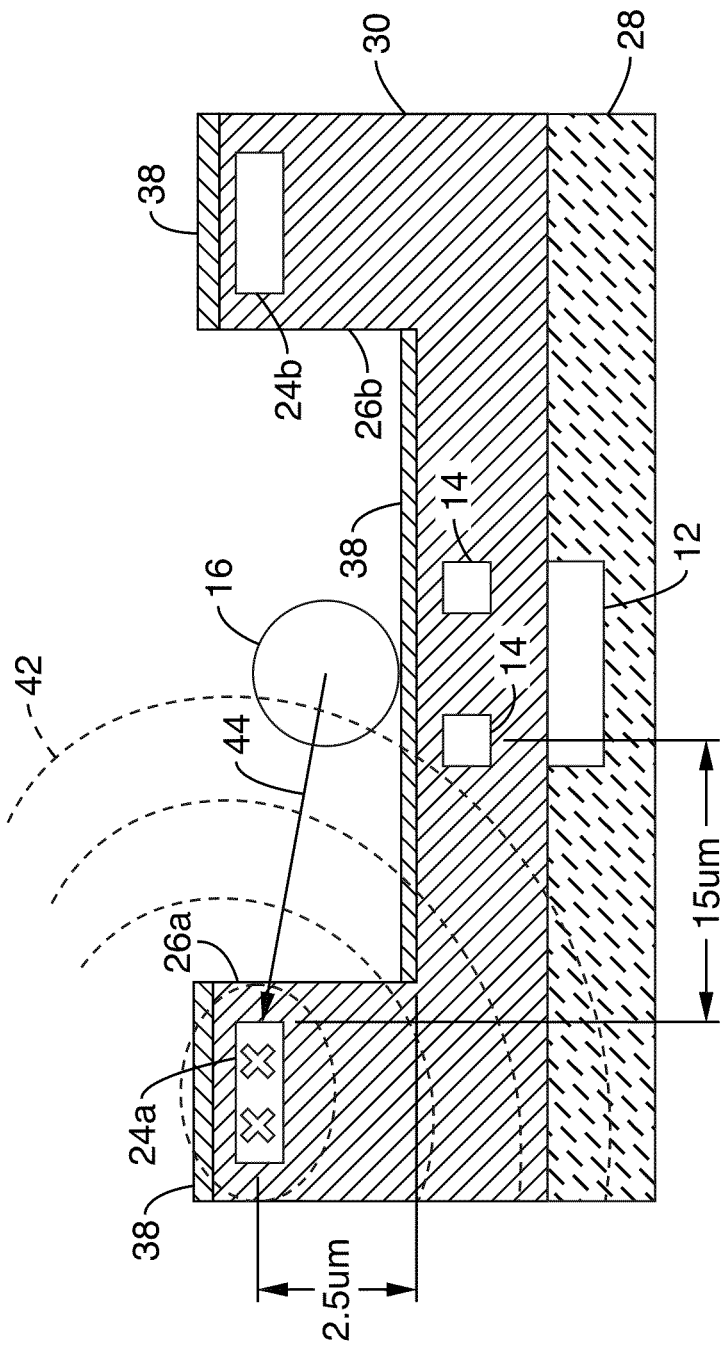
FIG. 7 is a partial cross-sectional schematic view of the array shown in FIG. 5, taken through the center of a micro-coil/Hall sensor pair, illustrating the motion on a bead imparted by the magnetic force from the current line on the upper ridge of the trench, where the bead is moved away from the micro-coil/Hall sensor pair.
Figure 9:
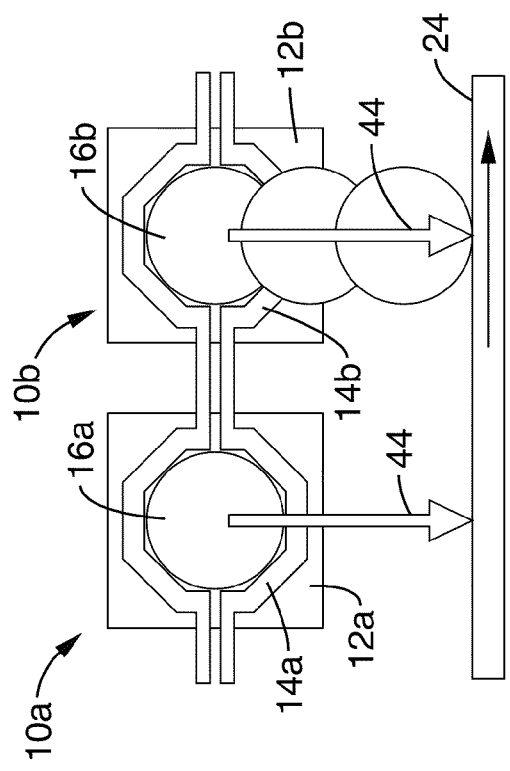
FIG. 9 is a schematic partial plan view of the array shown in FIG. 5, showing the non-specifically bound bead in FIG. 8 being removed due to the magnetic force imparted on the bead by a current line either embedded in the substrate or running along the upper ridge of the trench, and showing the specifically bound bead remaining in place.
Figure 8:
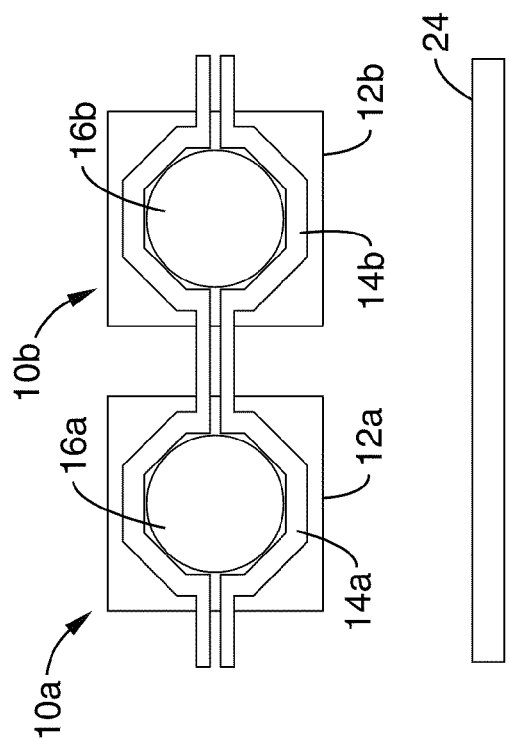
FIG. 8 is a schematic partial plan view of the array shown in FIG. 5, showing a specifically bound (e.g., biologically bound) bead and a non-specifically bound bead positioned above a micro-coil/Hall sensor pair.
Figure 10:
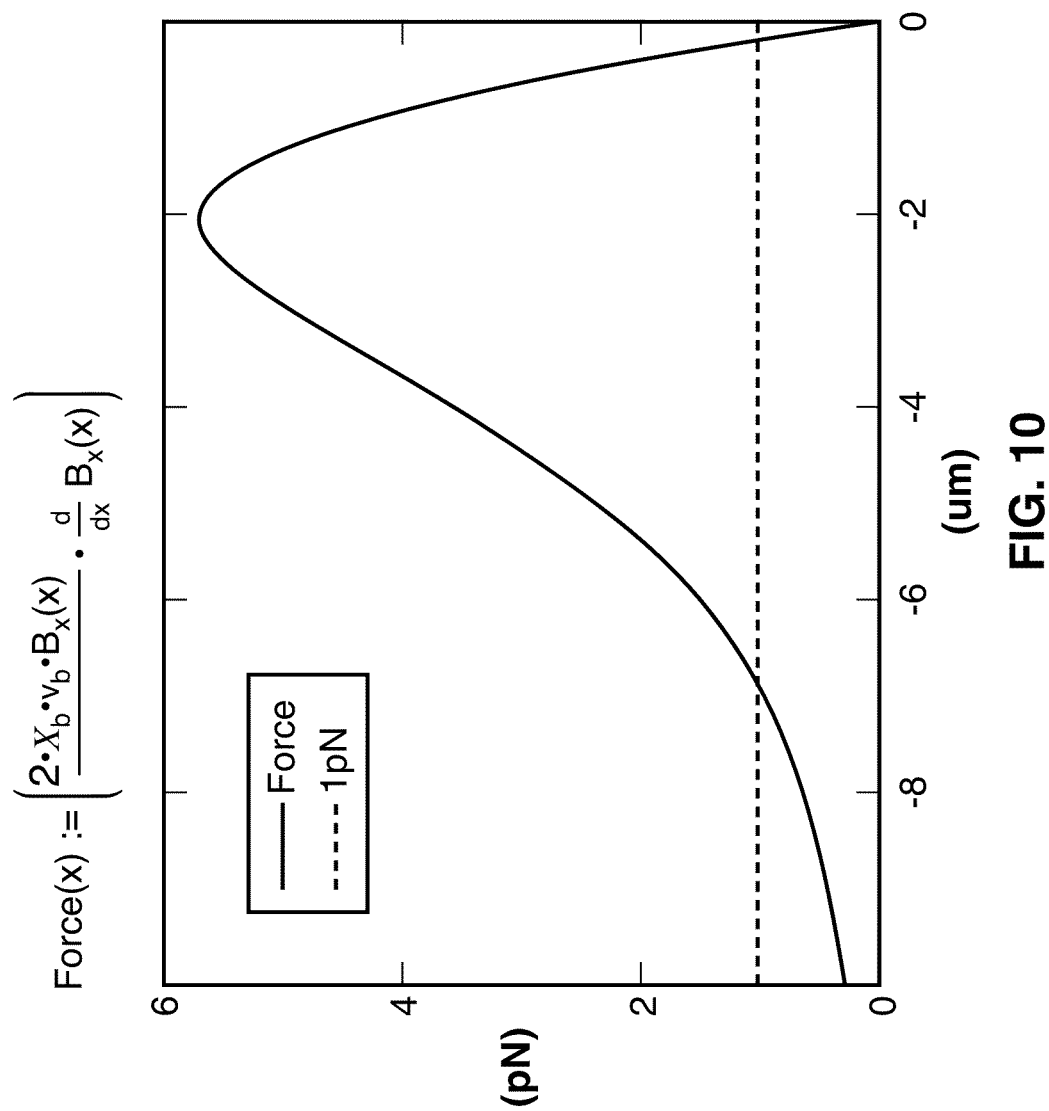
FIG. 10 is an example of a force-distance curve corresponding to the array shown in FIG. 9.

Referring also to FIG. 7 through FIG. 10, the current lines 24 are placed above the plane of the beads to eliminate the component of the force that pull the beads down into the plane of the IC, thus improving the magnetic separation efficiency. In the embodiment shown, the current lines are placed approximately 2.5 μm above the surface 18 of the substrate. FIG. 7 illustrates the leftmost current line being turned on while the rightmost current line is turned off. The double X's in the leftmost current line 24a denote the current flow into the paper; the rightmost current line 24b is not energized. The magnetic field 42 generated by the leftmost current line creates a magnetic force 44 which imparts motion to the bead and causes the bead to be moved away from the micro-coil/Hall sensor pair and toward the side of the trench. Optionally, the current can be alternated between the left current line 24a and the right current line 24b by arbitrary digital modulation. FIG. 8 is a schematic partial plan view of the array shown in FIG. 5, illustrating a specifically bound bead 16a and a non-specifically bound bead 16b positioned above a micro-coil/Hall sensor pair 10a, 10b, respectively, and in relation to a current line 24. FIG. 9 is a schematic partial plan view of the array shown in FIG. 5, showing the non-specifically bound bead 16b in FIG. 8 being removed due to the magnetic force 44 imparted on the bead by the current line 24 in the upper ridge portion of the trench sidewall and the specifically bound 16a bead remaining in place. FIG. 10 is an example of a force-distance curve corresponding to the array shown in FIG. 9.

Figure 11:
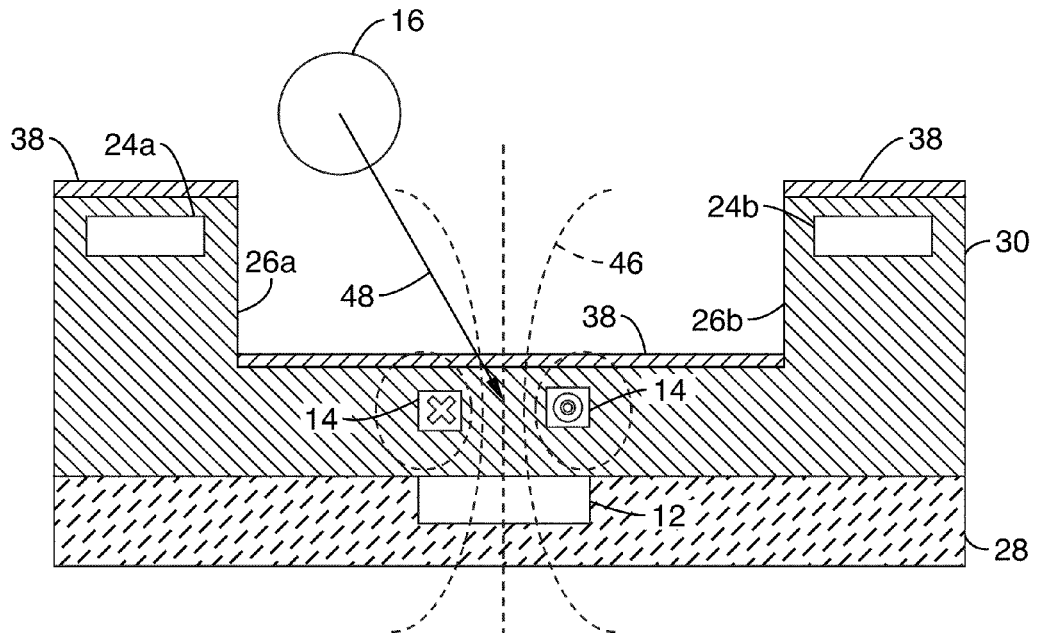
FIG. 11 is a partial cross-sectional schematic view of the array shown in FIG. 5, illustrating the motion on a bead imparted by the magnetic force from a micro-coil, where the bead is moved into position over the Hall sensor/micro-coil pair.

Note that if the magnetic beads settle too far from the sensors they will not be detected. Accordingly, in the preferred embodiment, current carrying conductors are placed in the substrate, for example in the same plane as the micro-coils. Even more preferably, the micro-coils 14 are used as these current carrying conductors as illustrated in FIG. 11. In FIG. 11, the X and circle-dot in the micro-coil 14 indicate current flow in the micro-coil into the paper and out of the paper, respectively. A magnetic field 46 is generated by the micro-coil 14, and motion on the bead 16 is imparted by the magnetic force 48 which results in bead being moved into position over the micro-coil/Hall sensor element. Here, the current lines in the upper ridge portions of the trench sidewalls are not energized but, instead, current passing through the micro-coils generates magnetic forces that pull the magnetic beads settling out of solution directly over the sensor area.

Figure 12:
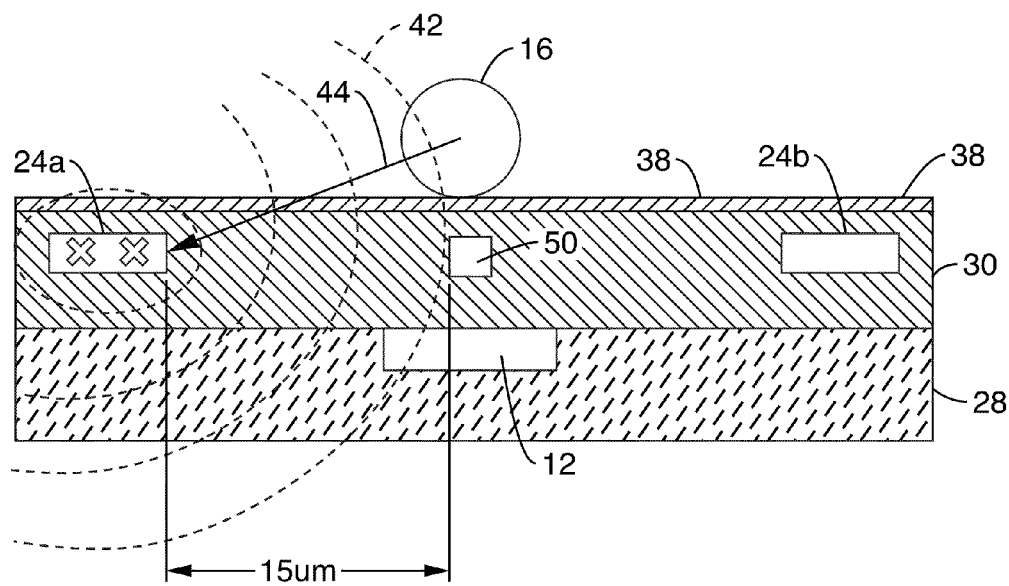
FIG. 12 is a partial cross-sectional schematic view of a "trenchless" embodiment of a sensor array according to the present invention, illustrating the motion on a bead imparted by the magnetic force from the separation current line embedded in the substrate, where the bead is moved away from a concentration/magnetization current line.

FIG. 12 through FIG. 16 illustrate that the invention can be embodied in various other ways. For example, FIG. 12 illustrates an essentially "trenchless" embodiment, since there are no sidewalls within which to place the separation field generating means. Accordingly, instead of being placed in the upper ridge portion of a trench sidewall, the separation field generating means, current line 24, is shown embedded beneath the surface of the substrate in the same plane as concentration/magnetization field generating means. In addition, FIG. 12 shows that, instead of being a plurality of micro-coils, the concentration/magnetization field generating means can be a current line 50 placed above the field detecting means 12 and running along the length of the substrate. These configurations, however, are functionally equivalent to the previously-described embodiments.

Figure 13:
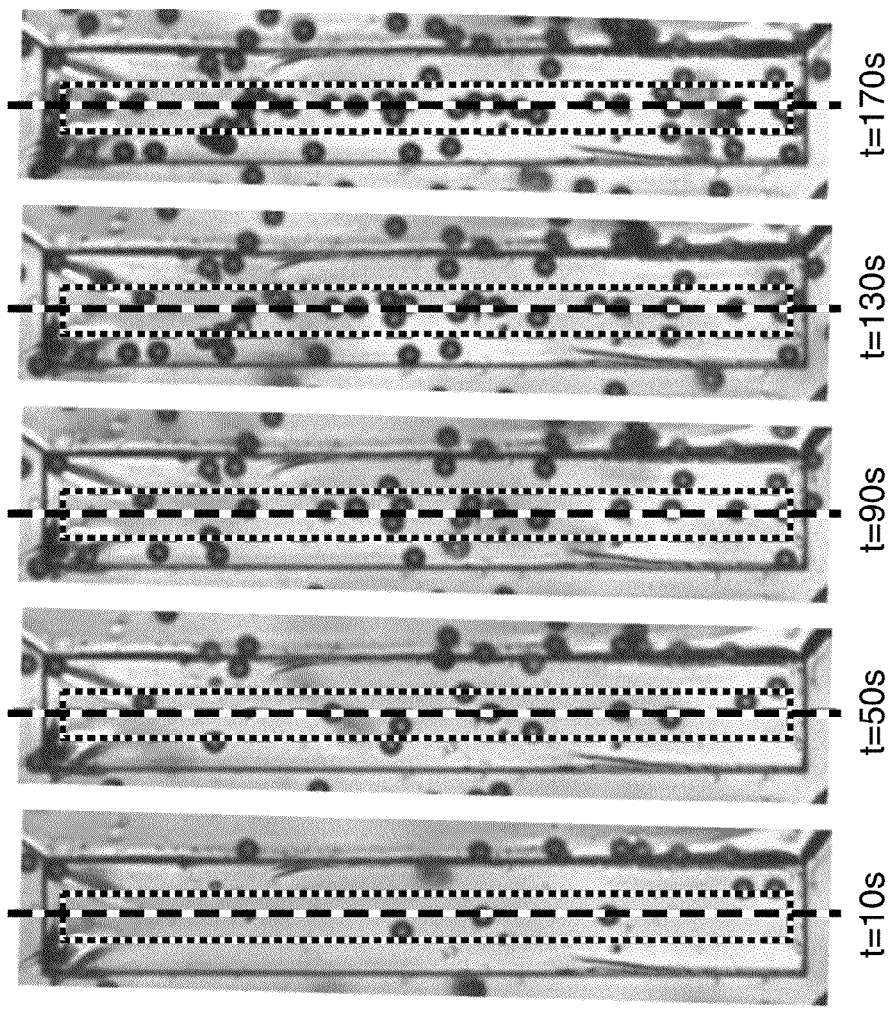
FIG. 13 is a series of micrograph plan views showing magnetic beads being pulled to the sensor area over time.

For example, current line 50 will generate a concentration/magnetization field as described above. FIG. 13 is a series of micrograph plan views showing the magnetic beads being pulled to the sensor area over time. As can be seen, the magnetic beads concentrate directly above the sensor area as current is passed through the current line 50. The current generates magnetic forces that pull the beads settling out of solution to the sensor area. To produce the effect shown in FIG. 13, we passed 3 mA of current through the current line (centermost dashed line) so as to pull the magnetic beads that are settling to the surface over the sensor area bounded by the outer dashed lines. The same effect would result from energizing micro-coils as previously described.

Figure 15:
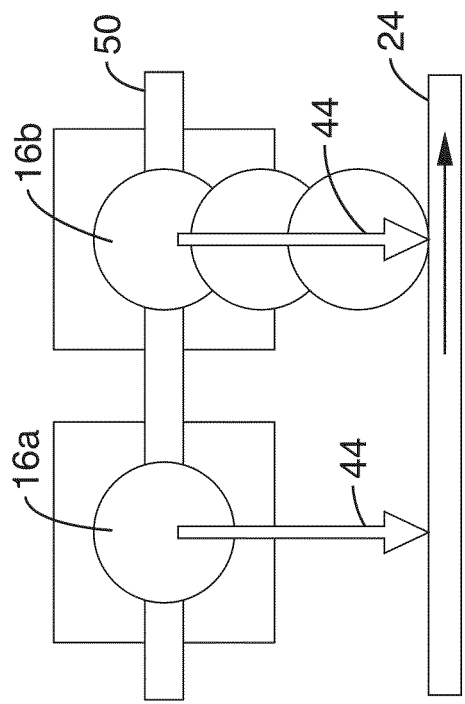
FIG. 15 is a schematic partial plan view of the array shown in FIG. 12, showing the non-specifically bound bead in FIG. 14 being removed due to the magnetic force imparted on the bead by a current line either embedded in the substrate and showing the specifically bound bead remaining in place.
Figure 14:
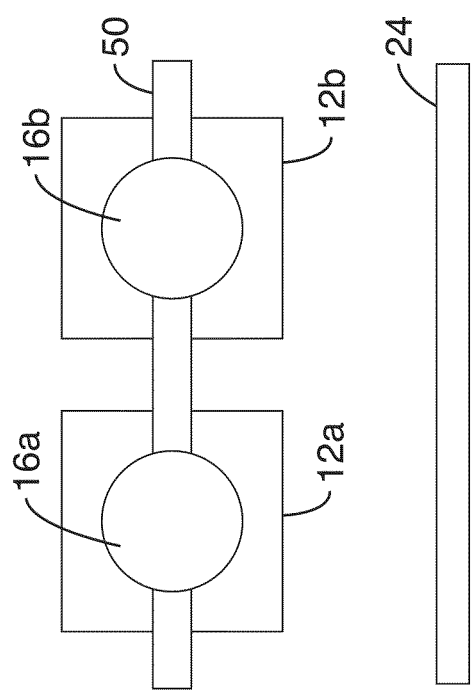
FIG. 14 is a schematic partial plan view of the array shown in FIG. 12, showing a specifically bound (e.g., biologically bound) bead and a non-specifically bound bead positioned above Hall sensors.
Figure 16A:
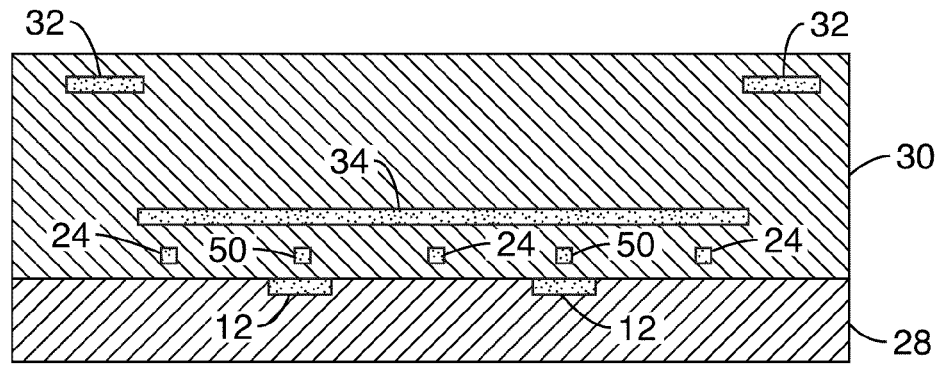
FIG. 16A through FIG. 16E is a cross-sectional flow diagram showing an embodiment of a reactive ion etching process used in fabrication of the integrated circuit shown in FIG. 12.
Figure 16B:
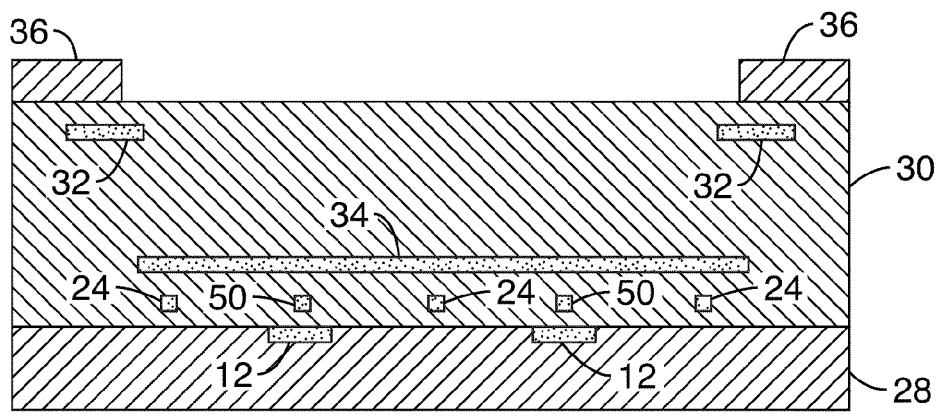
Figure 16C:
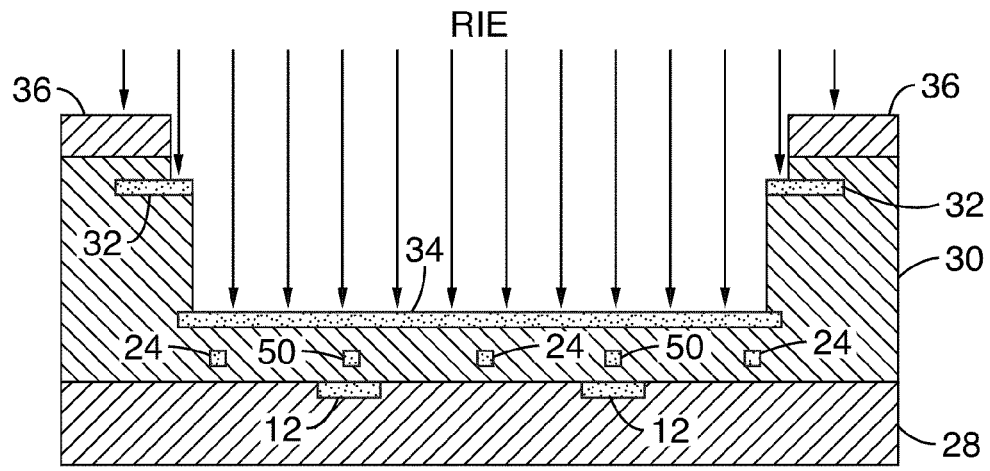
Figure 16D:
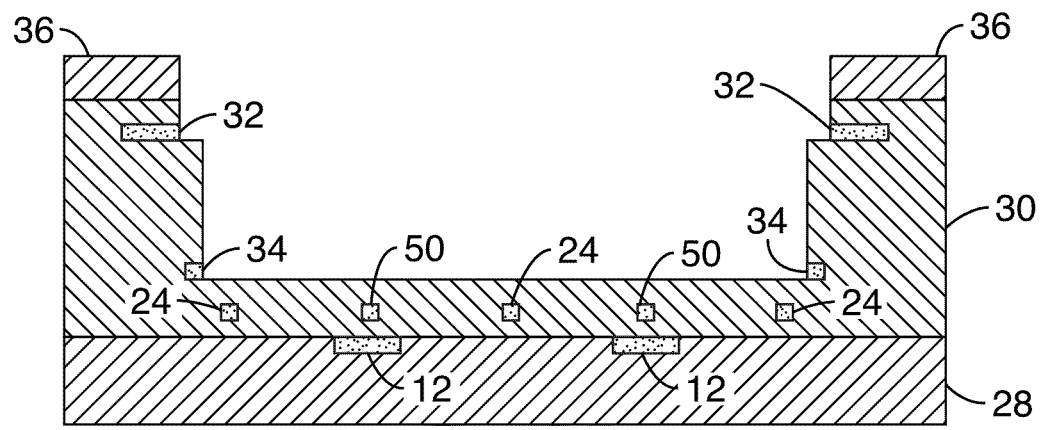
Figure 16E:
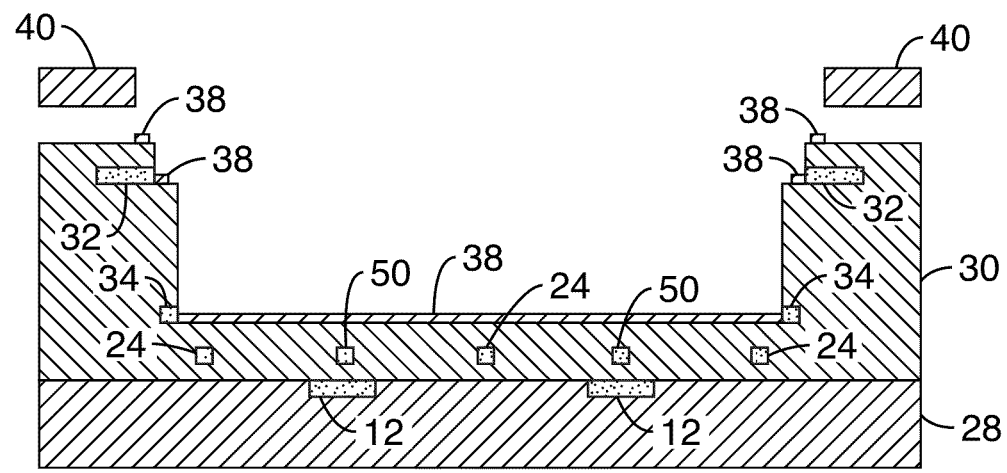

Furthermore, current line 24 will remove non-specifically bound beads as described above. For example, FIG. 14 illustrates a specifically bound bead 16a and a non-specifically bound bead 16b positioned above Hall sensors 12a, 12b, respectively, and in relation to the current line 50. FIG. 15 illustrates the non-specifically bound bead 16b in FIG. 14 being removed due to the magnetic force 44 imparted on the bead by the current line 24.

As indicated above, FIG. 12 illustrates an essentially "trenchless" embodiment, since there are no sidewalls within which to place the separation field generating means. In this regard, by "trenchless" we means that the individual rows of sensors in a multiple row IC are not separated by sidewalls. This is illustrated in FIG. 16 which shows an example fabrication process for an IC with two sensor rows. The processing would follow steps similar to those described in relation to FIG. 6. Those of ordinary skill in the art will readily understand the details of the process shown in FIG. 16 from the discussion of FIG. 6 and description of the IC above.

For the foregoing discussion, it should be appreciated that the combination of magnetic separation field generating means such (e.g., current lines) and the magnetic concentration/magnetization field generating means (e.g., current lines; micro-coils) embedded in the substrate above the sensors beneficially allows for manipulation of the magnetic beads. Beads can be moved away from the sensors or concentrated over the sensors by energizing either the separation field generating means or the concentration/magnetization field generation means.

By energizing the concentration/magnetization field generating means, but not the separation field generating means, all of the beads can be concentrated above the sensor area, where at least a portion of the beads will specifically bind to the surface of the trench. In one exemplary mode of operation, the concentration/magnetization field generating means is then turned off and the separation field generating means is turned on to displace (e.g., magnetically wash) the non-specifically bound beads from above the sensors. Once the non-specifically bound beads are removed by the magnetic forces generated by the separation field generating means, the separation field generating means is turned off, and the concentration/magnetization field generation means is turned on again to magnetize the specifically bound beads that remain. The field detecting means simultaneously detects the specifically bound beads that are magnetized by the concentration/magnetization field generating means.

Optionally, in another exemplary mode of operation, we can leave the separation field generating means turned on during the detection process to prevent non-specifically bound beads that were previously removed from the sensor area from being drawn back to the sensor area due to the forces generated by the current through the concentration/magnetization field generating means. Further, we can optionally switch current to separation field generating means on either side of the sensor at a variable frequency so that the non-specifically bound beads are pulled to either side of the sensor area and not just in one direction. The separation field generating means can be kept energized during detection, with the current flowing through them at the same or different frequency than the current through the concentration/magnetization field generating means. Detection can be performed at the same time as the washing to obtain a real time analysis of the washing effectiveness.

Referring now to FIG. 17, for use in biosensing and other applications, the integrated circuit 20 would necessarily employ electrical connections to external devices. To facilitate use in such applications, the integrated circuit would preferably be flip chip bonded to one side of a printed circuit board (PCB) 200 as illustrated in FIG. 17. In this embodiment, the printed circuit board has a hole 202 between both sides to allow biological fluids pass through the hole from the other side of the circuit board to reach the surface of the IC.

Figure 19:
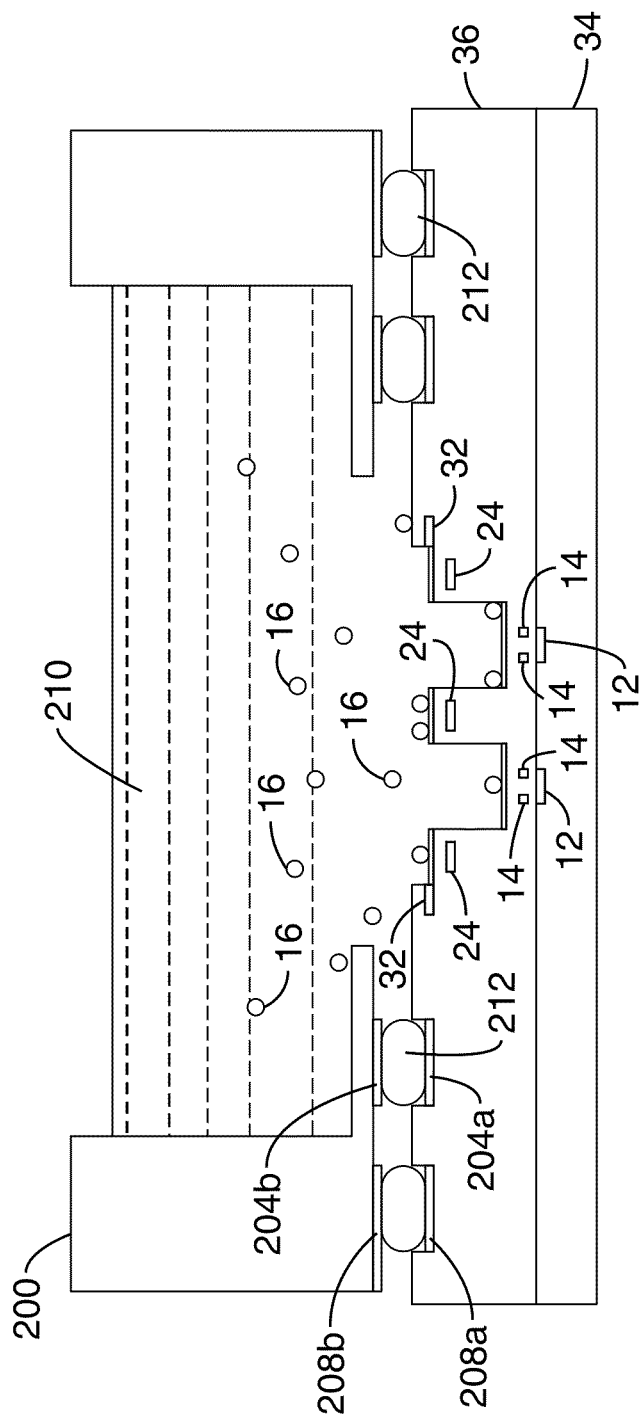
FIG. 19 is a partial cross-sectional schematic view of the circuit board shown in FIG. 17 with an attached integrated circuit shown in FIG. 18, and illustrating a seal ring to prevent leakage of a biological fluid.

Referring also to FIG. 18 and FIG. 19, a metal ring 204a preferably surrounds the sensor area 206 to isolate the connection pads 208a on the IC and corresponding connection pads 208b on the PCB from the biological fluid 210 to which the sensor area 206 is exposed. This metal ring is preferably solder bumped and soldered to a corresponding ring 204b on the printed circuit board. The IC is flip-chip bonded to the bottom of the PCB in a way that simultaneously bonds the connection pads and the solder ring with solder bumps 212. This allows the sensor area 206 to be exposed to the biological fluid 210 via hole 202, but keeps the biological fluid isolated from the electrical connections 208. As can be seen, the solder seal ring encircles the sensor area, thus inhibiting the biological fluid from short-circuiting the electrical connections.

Figure 20:
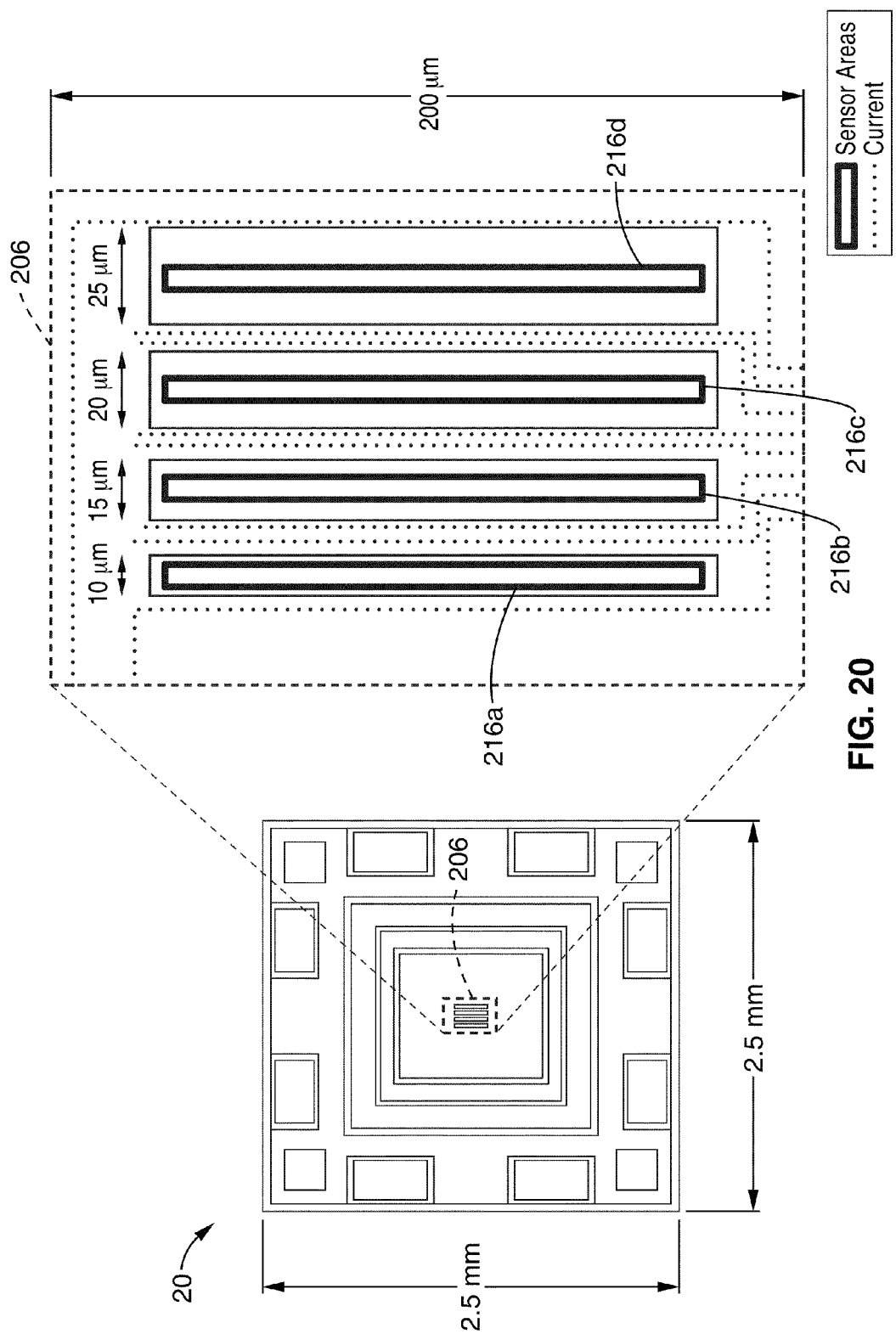
FIG. 20 illustrates an integrated circuit as shown in FIG. 18 with the sensor area having four trenches of varying width.

Referring again to FIG. 17, in one embodiment the PCB 200 is configured as a removable cartridge having printed connector pads 214 at one end for mating with a corresponding socket. Accordingly, the aforementioned printed circuit board with a flip bonded IC on one side can, for example, be a component of a cartridge-based blood assay system. In one embodiment, a vial is seated into a holder on the opposite side of the circuit board, with the circuit board end of the vial opening into the hole to the surface of the IC. The opposite end of the vial would have a mouth with a cap, plug or other type of sealing lid to allow fluid to be contained in the vial. This assembly forms a cartridge that can be used for the assay. In one embodiment, the sensor area comprises multiple arrays. FIG. 18 and FIG. 20 illustrate the integrated circuit with a sensor area 206 that comprises four sensor arrays 216a, 216b, 216c, and 216d of varying widths to sense different biological components. In the example shown, the widths of sensor arrays 216a, 216b, 216c and 216d are 10 µm, 15 µm, 20 µm and 25 µm, respectively, and the trenches are 200 µm in length.

Using the above-described cartridge, for example, the following exemplary protocol can be followed for the assay of whole blood.

(a) When ready to run assay, the user inserts the cartridge into a reader and initiates a calibration process.

(b) After calibration is complete, whole blood is taken from a finger prick and placed onto a membrane filter at the mouth of the vial.

(c) The user then closes the lid to the vial and agitates the contents of the vial by turning it over several times for approximately 30 seconds.

(d) As the solution in the vial is agitated, the target analyte diffuses through the membrane filter into the vial.

(e) Magnetic beads in the vial, conjugated with one or more bio-chemical agents stick specifically to the target analyte that has diffused in the vial.

(f) The magnetic beads settle to the surface of the IC which is also coated with one or more bio-chemical agents that binds to the analyte.

(g) The beads that settle to the surface of the IC but that are not tethered to the surface specifically via a strong biochemical complex are removed by magnetic forces generated on-chip.

(h) The remaining beads are strongly tethered to the surface of the IC are detected by an array of integrated magnetic sensors embedded in the substrate.

(i) The signal from the beads are processed on-chip and posted on the reader's display.

In another embodiment, the magnetic beads would first be incubated in a separate vial with the filtered raw sample before being introduced in the vial containing the detection IC.

Preferably, the sample to be assayed is first prepared for separating the species to be assayed from interfering agents. This can be carried out, for example, using a membrane filter to block particulate matter such as whole blood cells from physically interfering with the on-chip assay. Other approaches include using (a) an immunochromatographic strip, (b) fluid delivery systems such as microfluidics or patterned capillary channels, (c) conventional centrifugation, and (d) column chromatography. Sample preparation systems such as membrane filters and immunochromatographic strips can be augmented by chemical functionalization to block interfering agents, much like column chromatography.

Example

Figure 21B:
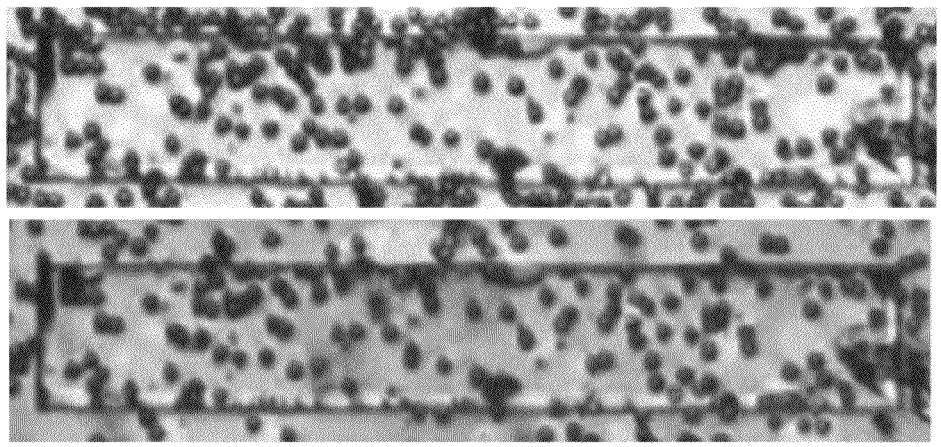
FIGS. 21A and 21B are micrographs showing negative and positive control of purified human IgG assay, respectively.
Figure 21A:
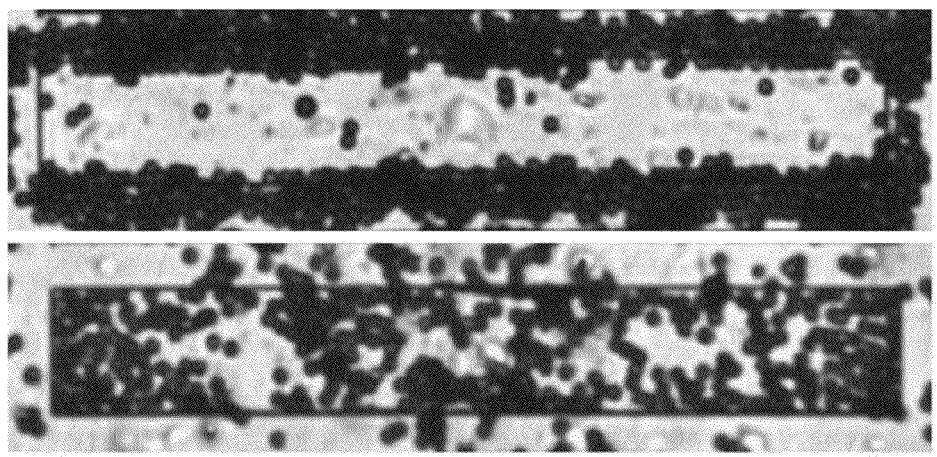
Figure 22B:
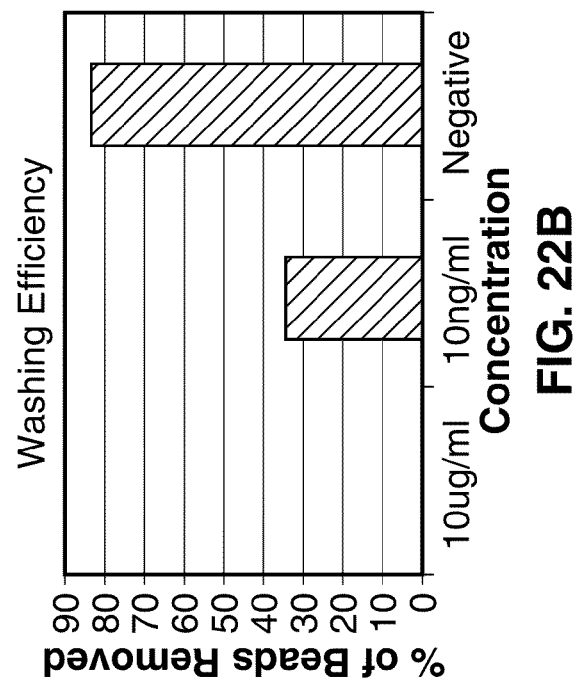
FIGS. 22A and 22B are graphs showing on-chip assay results and washing efficiency, respectively.
Figure 22A:
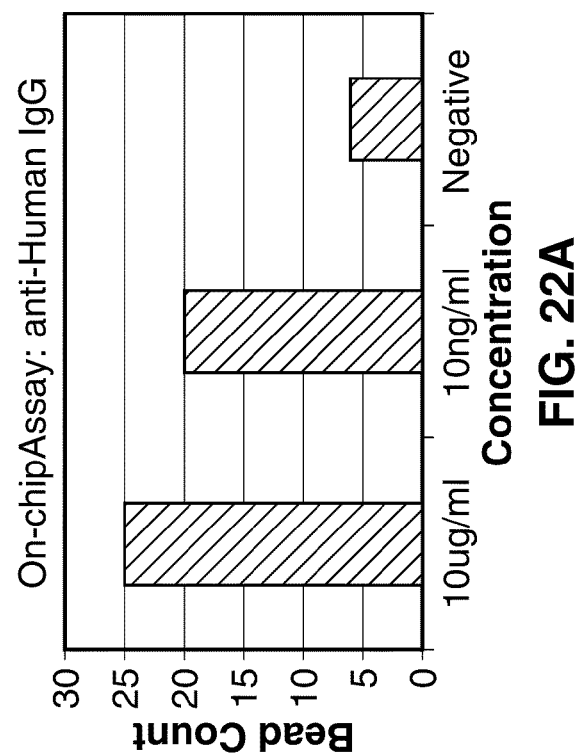

In a functionalization experiment, we evaporated gold on the surface of the IC and an Fc specific anti-Human IgG was physio-adsorbed on the surface. FIG. 21A shows the negative control that ensures that nonspecifically bound beads are removed during magnetic separation; a solution of purified Human IgG was incubated and the excess IgG was washed away. A primary biotinylated Fab specific anti Human IgG was added. Lastly the streptavidin coated 2.8 µm beads were added and let to incubate. Here, 50 mA of current was passed through the current lines generating a force of 2 pN at the center of the trench. 99% of specifically bound beads remained stationary. FIG. 21B shows the positive control that ensures that specifically bound beads remain stationary during magnetic separation. The protocol is the same as the positive control, with the exception that the Human IgG is never added. Results show that 99% of non-specifically bound beads are removed. FIGS. 22A and 22B are graphs showing on-chip assay results and washing efficiency, respectively. Note that the surface functionalization scheme described above is just an example. Gold does not necessarily have to be deposited, and other chemical binding agents can also be used to attach antibodies or other chemical species to the surface.

Accordingly, this biosensor is particularly well suited for determining the concentration of infectious disease agents in blood or serum.

Figure 23:
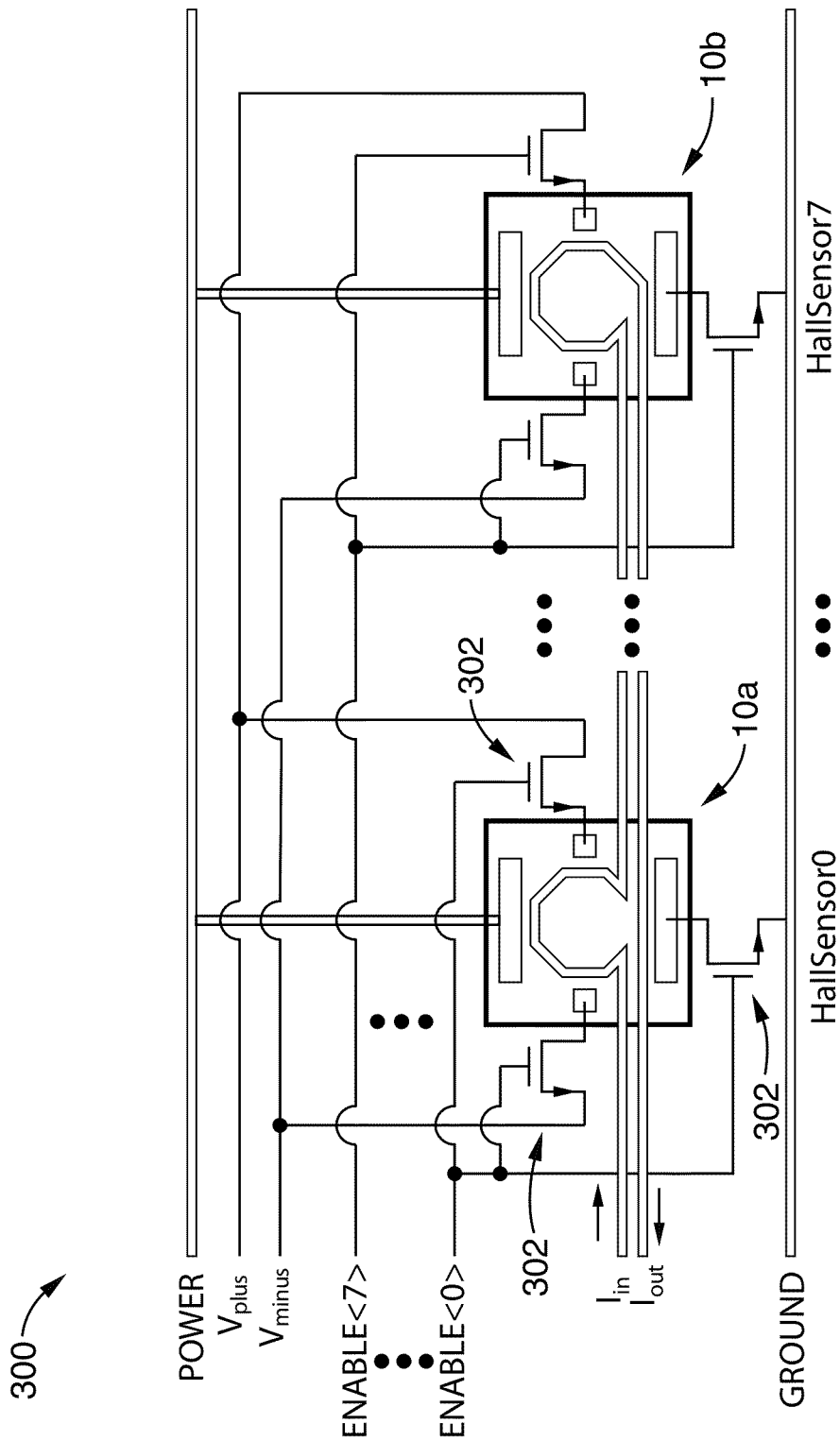
FIG. 23 is an electrical circuit diagram of a bank of eight micro-coil/Hall sensor elements according to an embodiment of the invention.

It will be appreciated that the micro-coil/Hall sensor elements can be connected in various circuit configurations. For example, FIG. 23 illustrates a circuit 300 comprising a row of eight serially connected micro-coil/Hall sensor elements in a single trench. While current runs through all the micro-coils within the row at the same time, the Hall sensors are individually addressable for detection of individual magnetic beads. In other embodiments, multiple Hall sensors can be activated at the same time. The signal from the Hall sensors can be read out in parallel or multiple magnetization frequencies can be used in a frequency division multiplexing scheme. Each Hall sensor is connected to three NMOS switches 302, one for the power supply and two for the differential magnetic signal. When a Hall sensor is activated, all of the switches are activated. Other configurations are possible with additional or fewer switches. The key is that each Hall sensor is individually addressable, and that several Hall sensors can be addressed and activated at the same time. Also, multiple concentration/magnetization lines or micro-coils can be activated at the same time and multiple separation lines can be activated at the same time.

Note also that an IC with multiple banks can be configured in an electronically addressable array so that each IC can also perform multiplexed assays since the array is addressable and different portions of the array can be functionalized with different bio-chemical agents. The magnetic concentration, the magnetic separation the fine detection resolution and high level of integration offered by this system combine for a detection mechanism that is rapid, accurate, easy to use and inexpensive. We anticipate that one hundred twenty eight micro-coil/Hall sensor elements with parallelized reading and integrated magnetic washing of non specific biological interactions would be combined into a fully integrated bio-assay platform.

For example, FIG. 24 illustrates a circuit 400 with sixteen instances (e.g., sixteen banks or rows) of the circuit 300 shown in FIG. 23 to create an 8×16 array for a total of one-hundred twenty-eight micro-coil/Hall sensor elements. The digital logic for addressing and decoding are integrated on-chip. The signal from a Hall sensor in the sensor array is subtracted from the signal of a dummy Hall sensor that cannot have any beads above it. The array of dummy Hall sensors, while not shown here, is placed away from the sensor area that is exposed to fluid. Various addressing schemes are also shown on the left in FIG. 24. Preferably, the current lines for generating the magnetic forces for removing the non-specifically bound beads are placed along the ridges of the etched trenches, adjacent to the row of eight micro-coil/Hall sensor elements, as illustrated in FIG. 25. The dashed lines surrounding the rows of Hall micro-coil/Hall sensor elements indicate the area of the etched out trench portions.

From the foregoing, it will be appreciated that the platform described can be used for many applications, including, but not limited to, the following.

1. Diagnostics:
   (a) Viral vs. bacterial infections;
   (b) Parallel or multiplexed assays;
   (c) DNA micro-array;
   (d) Oral bacteria screenings;
   (e) Glucose, cholesterol, metabolites, small molecules etc.
2. Environmental assays:
   (a) Food contamination;
   (b) Water/soil contamination.
3. Proteomics:
   (a) Protein-protein binding force measurements;
   (b) Protein-protein binding resonant frequencies;
   (c) DNA methylation.
4. Magnetic Bead AFM:
   (a) No 1/f noise at low frequencies;
   (b) Force and frequency digitally controlled.
5. Magnetic Bead Characterization:
   (a) Explore magnetic properties of single beads of different sizes and with different magnetic nano-particles.
6. Low Cost Bio-sensor Networks:
   (a) Integrated transmitter can send assay results directly to base station for statistical analysis;
   (b) Real-time outbreak/contamination monitoring.
7. Magnetic sensor Arrays:
   (a) Magnetic field and magnetic gradient field quantization.

The appeal of this system can be understood by analyzing the results in the proper context of what we consider makes a good bio-sensor:

1. Cost—Biological contamination concerns dictate that Point-of-Care sensor cartridges be disposable, thus putting a premium on low cost implementations. From an overall system perspective, CMOS is the most cost effective option since it allows the integration of the sensor front-end with the necessary signal processing back end.

2. Speed—The current detection time of $\tau=1$ s can be reduced by compromising the abundant SNR. For a large array of sensors, CMOS also has the distinct advantage of offering highly parallelized readout at low cost. In addition to parallel hardware, multiple magnetization frequencies can be used in a frequency division multiplexing scheme to further speed up the detection time.

3. Ease-of-Use—Integration is the crux to simplifying the bio-sensor protocol. Integrated bead detection is one necessary component, the other being integrated magnetic separation for the elimination of non-specific biological interactions. In the fully integrated scenario, the minimum diameter of the bead chosen for bio-sensing applications will be determined by the maximum magnetic forces that can be applied to it, and not by the intrinsic detection sensitivity limit of the sensor technology. The design versatility and high level of integration offered by CMOS are advantageous in this context.

4. Sensitivity—Bio-sensor sensitivity and detector resolution are not synonymous and biosensor sensitivity may be limited ultimately by mass transport effects. This issue is addressed by implementing a dense array of sensors/actuators, each capable of magnetically drawing a bead to its surface and then detecting it. The dynamic range of such a system depends on the total number of elements in the array, which is maximized in CMOS at low cost.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

TABLE 1

Calculated Simulated and Measured Z-Component of the Applied Coil Field and Bead Magnetization Field, Observed from the Plane of the Hall Sensor

|  | Calculated | Simulated | Measured |
| --- | --- | --- | --- |
| $B_{applied}(Z_{Hall})$ | 750 µT | 770 µT | 488 µT* |
| $B_{bead,z}(Z_{Hall})$ | 10.2 µT | 8.6 µT | 10.8 µT |

*Underestimated since the coil field is highly non-uniform.

What is claimed is:

1. An integrated circuit apparatus, comprising:
a dielectric substrate having an exposed surface area;
means for generating a separation field; and
means for detecting a magnetic field;
said magnetic field detecting means embedded in the dielectric substrate beneath the exposed surface area;

said separation field generating means comprising at least one current line embedded in the dielectric substrate beneath the exposed surface area and between the field detecting means and the exposed surface area, said at least one current line being embedded in the dielectric substrate at a laterally spaced-apart position in relation to said magnetic field detecting means;

wherein at least a portion of the exposed surface area of the dielectric substrate is functionalized with a biochemical agent that binds with a target analyte; whereby magnetic particles configured to specifically bind with said target analyte are configured to bind specifically to said functionalized portion of the exposed surface area via the target analyte;

wherein the at least one current line is configured such that magnetic forces generated when current runs through the separation field generating means are sufficient to pull the unbound magnetic particles away from the functionalized portion of the exposed surface area; and wherein the magnetic field detecting means are provided for detecting specifically bound remaining magnetic particles on said functionalized portion of the exposed surface area.

2. An apparatus as recited in claim 1, further comprising:
means for generating a concentration/magnetization field;
said concentration/magnetization field generating means embedded in the substrate between said field detecting means and the exposed surface area.

3. An apparatus as recited in claim 2, wherein the separation field generating means is positioned in the same plane as the concentration/magnetization field generating means.

4. An apparatus as recited in claim 2, wherein the separation field generating means is positioned in a plane above the concentration/magnetization field generating means.

5. An apparatus as recited in claim 2, wherein the concentration/magnetization field generating means comprises a magnetic field generating element selected from the group consisting of a micro-coil, a current line, or other element that generates a magnetic field.

6. An apparatus as recited in claim 1, wherein the field detecting means comprises a magnetic field detecting element selected from the group consisting of a Hall sensor, variable inductance wire, or other element that senses a magnetized object.

7. An apparatus as recited in claim 1, wherein the field detecting means comprises a plurality of individual magnetic field detecting elements.

8. An apparatus as recited in claim 7, wherein at least a portion of the magnetic field detecting elements are addressable.

9. An apparatus as recited in claim 2, wherein the concentration/magnetization field generating means comprises a plurality of individual magnetic field generating elements.

10. An apparatus as recited in claim 2:
wherein the concentration/magnetization field generating means comprises a plurality of individual magnetic field generating elements;
wherein the field detecting means comprises a plurality of individual magnetic field detecting elements; and
wherein each magnetic field generating element is paired with a magnetic field detecting element to create a stacked unit cell.

11. An apparatus as recited in claim 10, where at least a portion of the unit cells are addressable.

12. An apparatus as recited in claim 1, wherein the apparatus is a component of a biosensor device.

13. An apparatus as recited in claim 1, wherein at least a portion of the exposed surface area of the substrate is functionalized with a biochemical agent that binds with a target analyte.

14. An apparatus as recited in claim 1, wherein the field detecting means is configured to detect immobilized magnetic particles.

15. An integrated circuit apparatus, comprising:
a dielectric substrate having a trench with an exposed surface area, the trench having a recessed region and a sidewall;
means for detecting a magnetic field; and
means for generating a magnetic separation field;
said magnetic field detecting means embedded in the dielectric substrate beneath the exposed surface area of the recessed region;
said separation field generating means comprising at least one current line embedded in the sidewall of the dielectric substrate at a laterally spaced-apart position in relation to said magnetic field detecting means;
wherein at least a portion of the exposed surface area of the dielectric substrate is functionalized with a biochemical agent that binds with a target analyte; whereby magnetic particles configured to specifically bind with said target analyte are configured to bind specifically to said functionalized portion of the exposed surface area via the target analyte;
wherein the at least one current line is configured such that magnetic forces generated when current runs through the separation field generating means are sufficient to pull the unbound magnetic particles away from the functionalized portion of the exposed surface area; and
wherein the magnetic field detecting means are provided for detecting specifically bound remaining magnetic particles on said functionalized portion of the exposed surface area.

16. An apparatus as recited in claim 15, further comprising:
means for generating a magnetic concentration/magnetization field;
said concentration/magnetization field generating means embedded in the substrate beneath the exposed surface area and between the field detecting means and the exposed surface area.

17. An apparatus as recited in claim 16, wherein the concentration/magnetization field generating means comprises a magnetic field generating element selected from the group consisting of a micro-coil, a current line, or other element that generates a magnetic field.

18. An apparatus as recited in claim 15, wherein the field detecting means comprises a magnetic field detecting element selected from the group consisting of a Hall sensor, variable inductance wire, or other element that senses a magnetized object.

19. An apparatus as recited in claim 15, wherein the field detecting means comprises a plurality of individual magnetic field detecting elements.

20. An apparatus as recited in claim 19, wherein at least a portion of the magnetic field detecting elements are addressable.

21. An apparatus as recited in claim 16, wherein the concentration/magnetization field generating means comprises a plurality of individual magnetic field generating elements.

22. An apparatus as recited in claim 16:
wherein the concentration/magnetization field generating means comprises a plurality of individual magnetic field generating elements;

wherein the field detecting means comprises a plurality of individual magnetic field detecting elements; and wherein each magnetic field generating element is paired with a magnetic field detecting element to create a stacked unit cell.

23. An apparatus as recited in claim 22, where at least a portion of the unit cells are addressable.

24. An apparatus as recited in claim 15, wherein the apparatus is a component of a biosensor device.

25. An apparatus as recited in claim 15, wherein at least a portion of the exposed surface area of the substrate is functionalized with a biochemical agent that binds with a target analyte.

26. An apparatus as recited in claim 15, wherein the field detecting means detects immobilized magnetic particles.

27. An integrated circuit apparatus, comprising:
a dielectric substrate having a plurality of trenches, each trench having a recessed region with an exposed surface area and a sidewall;
each trench comprising:
means for detecting a magnetic field; and
means for generating a magnetic separation field;
said magnetic field detecting means embedded in the dielectric substrate beneath the exposed surface area of the recessed region;
said separation field generating means comprising at least one current line embedded in the sidewall of the dielectric substrate at a laterally spaced-apart position in relation to said magnetic field detecting means;
wherein at least a portion of the exposed surface area of the dielectric substrate is functionalized with a biochemical agent that binds with a target analyte; whereby magnetic particles configured to specifically bind with said target analyte are configured to bind specifically to said functionalized portion of the exposed surface area via the target analyte;
wherein the at least one current line is configured such that magnetic forces generated when current runs through the separation field generating means are sufficient to pull the unbound magnetic particles away from the functionalized portion of the exposed surface area; and
wherein the magnetic field detecting means are provided for detecting specifically bound remaining magnetic particles on said functionalized portion of the exposed surface area.

28. An apparatus as recited in claim 27, further comprising:
means for generating a magnetic concentration/magnetization field;
said concentration/magnetization field generating means embedded in the substrate beneath the exposed surface area and between the field detecting means and the exposed surface area.

29. An apparatus as recited in claim 28, wherein the concentration/magnetization field generating means comprises a magnetic field generating element selected from the group consisting of a micro-coil, a current line, or other element that generates a magnetic field.

30. An apparatus as recited in claim 27, wherein the field detecting means comprises a magnetic field detecting element selected from the group consisting of a Hall sensor, variable inductance wire, or other element that senses a magnetized object.

31. An apparatus as recited in claim 27, wherein the field detecting means comprises a plurality of individual magnetic field detecting elements.

32. An apparatus as recited in claim 31, wherein at least a portion of the magnetic field detecting elements are addressable.

33. An apparatus as recited in claim 28, wherein the concentration/magnetization field generating means comprises a plurality of individual magnetic field generating elements.

34. An apparatus as recited in claim 28:
wherein the concentration/magnetization field generating means comprises a plurality of individual magnetic field generating elements;
wherein the field detecting means comprises a plurality of individual magnetic field detecting elements; and
wherein each magnetic field generating element is paired with a magnetic field detecting element to create a stacked unit cell.

35. An apparatus as recited in claim 34, where at least a portion of the unit cells are addressable.

36. An apparatus as recited in claim 27, wherein the apparatus is a component of a biosensor device.

37. An apparatus as recited in claim 27, wherein at least a portion of the exposed surface area of the substrate is functionalized with a biochemical agent that binds with a target analyte.

38. An apparatus as recited in claim 27, wherein the field detecting means detects immobilized magnetic particles.

39. An integrated circuit apparatus, comprising:
a dielectric substrate having an exposed surface area;
a separation field generator; and
a magnetic particle detector;
the magnetic particle detector embedded in the dielectric substrate beneath the exposed surface area;
said separation field generator comprising at least one current line embedded in the dielectric substrate beneath the exposed surface area and between the particle detector and the exposed surface area, said at least one current line being embedded in the dielectric substrate at a laterally spaced-apart position in relation to said magnetic particle detector;
wherein at least a portion of the exposed surface area of the dielectric substrate is functionalized with a biochemical agent that binds with a target analyte; whereby magnetic particles configured to specifically bind with said target analyte are configured to bind specifically to said functionalized portion of the exposed surface area via the target analyte;
wherein the at least one current line is configured such that magnetic forces generated when current runs through the separation field generator are sufficient to pull the unbound magnetic particles away from the functionalized portion of the exposed surface area; and
wherein the magnetic particle detector is provided for detecting specifically bound remaining magnetic particles on said functionalized portion of the exposed surface area.

40. An apparatus as recited in claim 39, further comprising:
a concentration/magnetization field generator;
said concentration/magnetization field generator being embedded in the substrate between said particle detector and the exposed surface area.

41. An apparatus as recited in claim 40, wherein the separation field generator is positioned in the same plane as the concentration/magnetization field generator.

42. An apparatus as recited in claim 40, wherein the separation field generator is positioned in a plane above the concentration/magnetization field generator.

43. An apparatus as recited in claim 40, wherein the concentration/magnetization field generator comprises a magnetic field generating element selected from the group consisting of a micro-coil, a current line, or other element that generates a magnetic field.

44. An apparatus as recited in claim 39, wherein the particle detector comprises a magnetic field detecting element selected from the group consisting of a Hall sensor, variable inductance wire, or other element that senses a magnetized object.

45. An apparatus as recited in claim 40, wherein the particle detector comprises a plurality of individual magnetic field detecting elements.

46. An apparatus as recited in claim 45, wherein at least a portion of the magnetic field detecting elements are addressable.

47. An apparatus as recited in claim 40, wherein the concentration/magnetization field generator comprises a plurality of individual magnetic field generating elements.

48. An apparatus as recited in claim 40:
wherein the concentration/magnetization field generator comprises a plurality of individual magnetic field generating elements;
wherein the particle detector comprises a plurality of individual magnetic field detecting elements; and
wherein each magnetic field generating element is paired with a magnetic field detecting element to create a stacked unit cell.

49. An apparatus as recited in claim 48, where at least a portion of the unit cells are addressable.

50. An apparatus as recited in claim 39, wherein the apparatus is a component of a biosensor device.

51. An apparatus as recited in claim 39, wherein at least a portion of the exposed surface area of the substrate is functionalized with a biochemical agent that binds with a target analyte.

52. An apparatus as recited in claim 39, wherein the particle detector is configured to detect immobilized magnetic particles.

\* \* \* \* \*